(12) United States Patent
Trieu et al.

(10) Patent No.: US 8,814,879 B2
(45) Date of Patent: Aug. 26, 2014

(54) ANNULUS REPAIR SYSTEMS AND TECHNIQUES

(75) Inventors: Hai H. Trieu, Cordova, TN (US); Lehmann K. Li, Milford, CT (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 158 days.

(21) Appl. No.: 13/301,027

(22) Filed: Nov. 21, 2011

(65) Prior Publication Data

US 2012/0065735 A1 Mar. 15, 2012

Related U.S. Application Data

(60) Division of application No. 11/731,334, filed on Mar. 30, 2007, now Pat. No. 8,075,618, which is a continuation of application No. 10/123,367, filed on Apr. 16, 2002, now Pat. No. 7,223,289.

(51) Int. Cl.
| | | |
|---|---|---|
| A61B 17/58 | (2006.01) | |
| A61B 17/60 | (2006.01) | |
| A61F 2/00 | (2006.01) | |
| A61B 17/70 | (2006.01) | |
| A61F 2/30 | (2006.01) | |
| A61F 2/46 | (2006.01) | |
| A61B 17/064 | (2006.01) | |
| A61F 2/28 | (2006.01) | |
| A61F 2/44 | (2006.01) | |

(52) U.S. Cl.
CPC ....... *A61F 2/442* (2013.01); *A61F 2310/00017* (2013.01); *A61F 2002/30299* (2013.01); *A61F 2002/4627* (2013.01); *A61F 2002/30461* (2013.01); *A61F 2002/30062* (2013.01); *A61F 2002/30074* (2013.01); *A61F 2002/30433* (2013.01); *A61F 2310/00365* (2013.01); *A61F 2002/4628* (2013.01); *A61F 2220/0066* (2013.01); *A61F 2210/0014* (2013.01); *A61F 2002/30785* (2013.01); *A61F 2/30965* (2013.01); *A61F 2002/30579* (2013.01); *A61F 2210/0057* (2013.01); *A61B 2017/0648* (2013.01); *A61F 2002/30448* (2013.01); *A61F 2250/0064* (2013.01); *A61F 2240/001* (2013.01); *A61F 2220/0041* (2013.01); *A61F 2/28* (2013.01); *A61F 2002/30459* (2013.01); *A61F 2002/4435* (2013.01); *A61F 2002/30841* (2013.01); *A61F 2220/0075* (2013.01); *A61B 17/0642* (2013.01); *A61F 2310/00329* (2013.01); *A61F 2002/2817* (2013.01); *A61F 2002/30578* (2013.01); *A61F 2002/30304* (2013.01); *A61F 2220/0025* (2013.01); *A61F 2002/30616* (2013.01); *A61F 2002/30451* (2013.01); *A61F 2220/005* (2013.01); *A61F 2220/0058* (2013.01); *A61F 2002/30387* (2013.01); *A61B 2017/0647* (2013.01); *A61F 2002/4623* (2013.01); *A61F 2002/30904* (2013.01); *A61F 2230/0063* (2013.01); *A61F 2002/30092* (2013.01); *A61F 2002/4495* (2013.01); *A61F 2002/30492* (2013.01); *A61B 17/70* (2013.01); *A61F 2002/30971* (2013.01); *A61F 2230/0093* (2013.01); *A61F 2310/00293* (2013.01); *A61F 2210/0004* (2013.01); *A61F 2310/00029* (2013.01); *A61F 2/4611* (2013.01); *A61F 2310/00023* (2013.01)
USPC .......................................................... 606/99

(58) Field of Classification Search
CPC .. A61F 2/4611; A61F 2/441; A61F 2002/444
USPC .................... 606/86 R, 99; 623/17.11–17.16, 623/13.11–13.15
See application file for complete search history.

(56) References Cited

U.S. PATENT DOCUMENTS

| | | | |
|---|---|---|---|
| 4,772,287 A | | 9/1988 | Ray et al. |
| 4,904,260 A | | 2/1990 | Ray et al. |
| 5,015,255 A | | 5/1991 | Kuslich |
| 5,147,374 A | | 9/1992 | Fernandez |
| 5,171,278 A | | 12/1992 | Pisharodi |
| 5,234,447 A | * | 8/1993 | Kaster et al. .................. 606/153 |

| | | | | | |
|---|---|---|---|---|---|
| 5,549,679 | A | 8/1996 | Kuslich | | |
| 5,562,736 | A | 10/1996 | Ray et al. | | |
| 5,645,568 | A | 7/1997 | Chervitz et al. | | |
| 5,681,310 | A | 10/1997 | Yuan et al. | | |
| 5,842,477 | A | 12/1998 | Naughton et al. | | |
| 5,895,426 | A | 4/1999 | Scarborough et al. | | |
| 5,976,186 | A | 11/1999 | Bao et al. | | |
| 6,004,347 | A | 12/1999 | McNamara et al. | | |
| 6,190,414 | B1 | 2/2001 | Young et al. | | |
| 6,224,630 | B1 | 5/2001 | Bao et al. | | |
| 6,245,107 | B1 | 6/2001 | Ferree | | |
| 6,273,852 | B1 | 8/2001 | Lehe et al. | | |
| 6,340,369 | B1 | 1/2002 | Ferree | | |
| 6,371,990 | B1 | 4/2002 | Ferree | | |
| 6,419,702 | B1 | 7/2002 | Ferree | | |
| 6,419,704 | B1 | 7/2002 | Ferree | | |
| 6,592,625 | B2 | 7/2003 | Cauthen | | |
| 6,652,585 | B2 | 11/2003 | Lange | | |
| 6,712,853 | B2 | 3/2004 | Kuslich | | |
| 2002/0007218 | A1 | 1/2002 | Cauthen | | |
| 2002/0123750 | A1 | 9/2002 | Eisermann et al. | | |
| 2002/0165542 | A1 | 11/2002 | Ferree | | |
| 2003/0004574 | A1 | 1/2003 | Ferree | | |
| 2004/0039392 | A1 | 2/2004 | Trieu | | |

FOREIGN PATENT DOCUMENTS

| | | |
|---|---|---|
| EP | 0 614 650 B1 | 12/1998 |
| WO | WO 96/10428 | 4/1996 |
| WO | WO 97/26847 | 7/1997 |
| WO | WO 99/61084 | 12/1999 |
| WO | WO 01/10316 | 2/2001 |
| WO | WO 01/12107 | 2/2001 |
| WO | WO 01/28464 A1 | 4/2001 |
| WO | WO 02/058599 | 8/2002 |
| WO | WO 02/064044 | 8/2002 |
| WO | WO 02/080821 | 10/2002 |

* cited by examiner

*Primary Examiner* — Sameh Boles

(57) ABSTRACT

Systems and methods for repairing annulus defects include at least one blocking member positionable in or adjacent to the annulus defect, at least one attachment portion for securing the blocking member to adjacent tissue, and instruments for placing and engaging the blocking member in and/or adjacent to the annulus defect. The blocking member extends at least partially across the annulus defect for repair of the defect and/or retention of nucleus material, one or more implants, bio-compatible materials or device, and/or other objects positioned in the disc space.

20 Claims, 17 Drawing Sheets

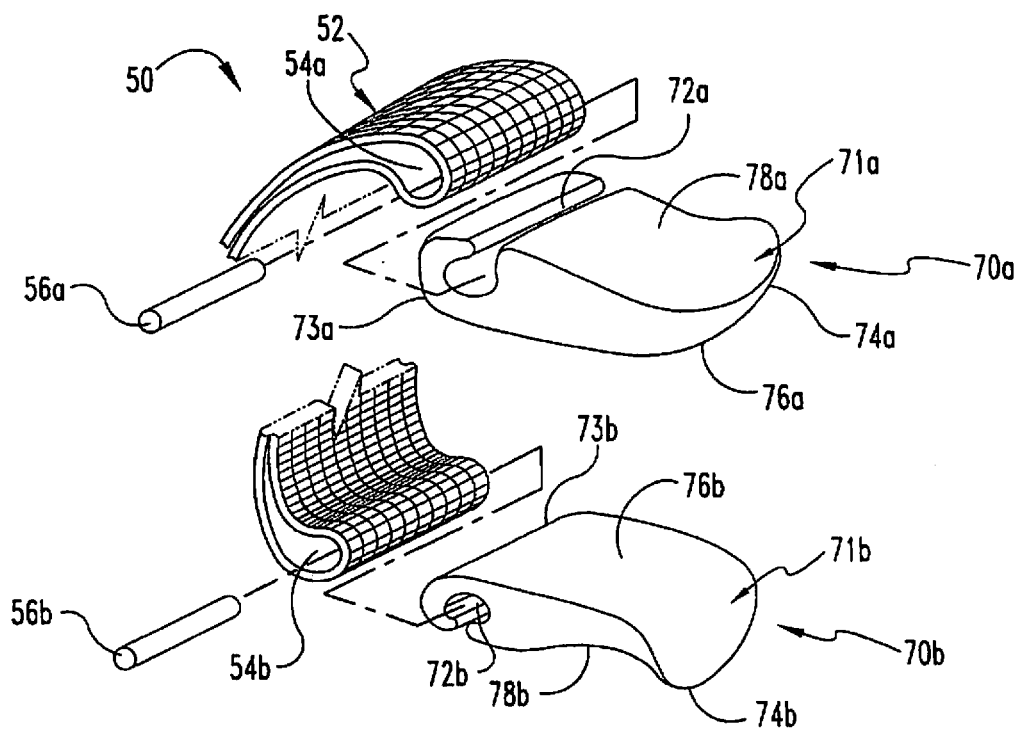
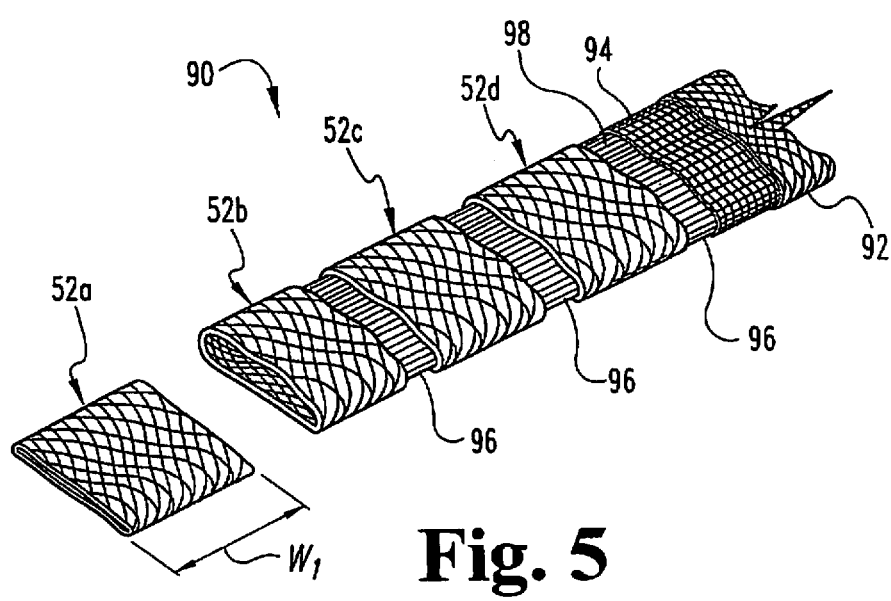

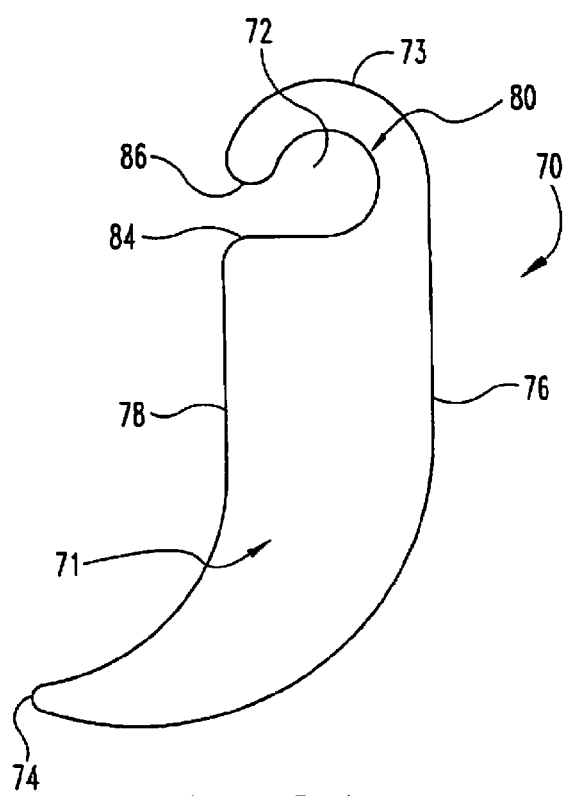
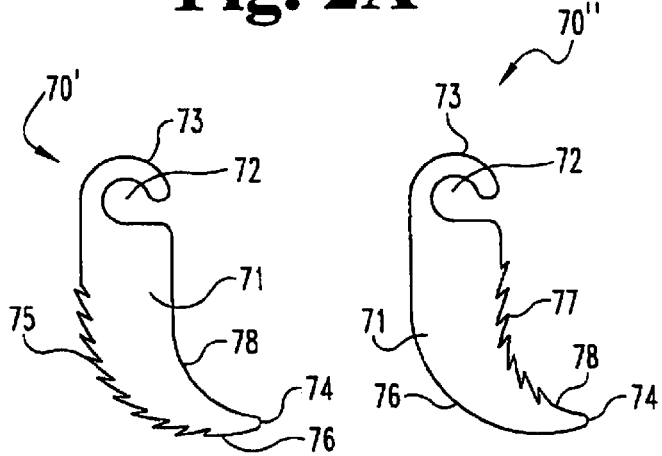
Fig. 2A
Fig. 2B  Fig. 2C
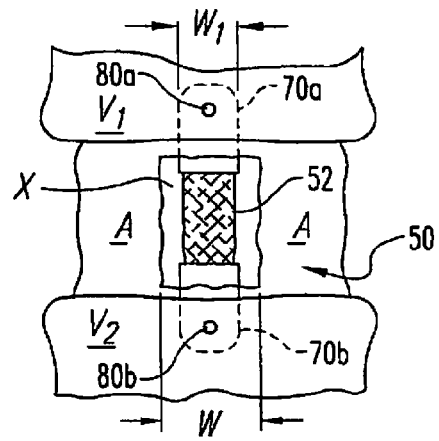
Fig. 4C
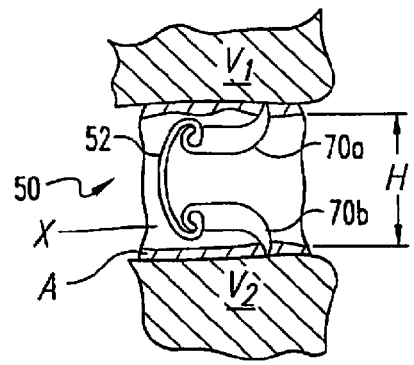
Fig. 4A
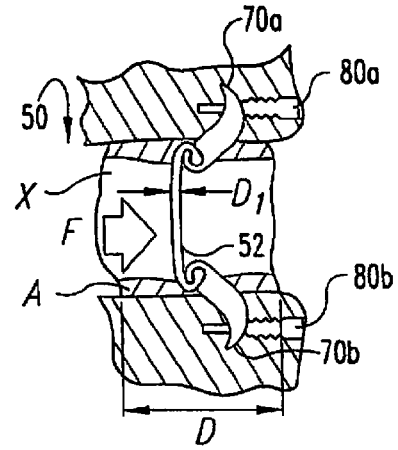
Fig. 4B

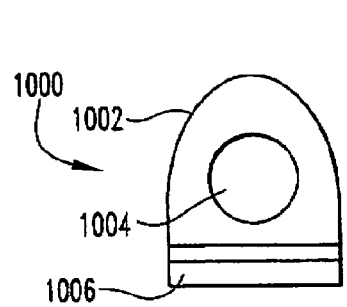 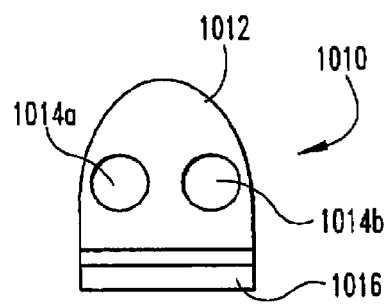
Fig. 3A  Fig. 3B
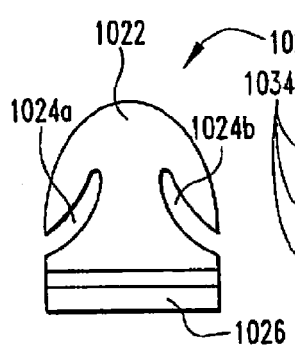 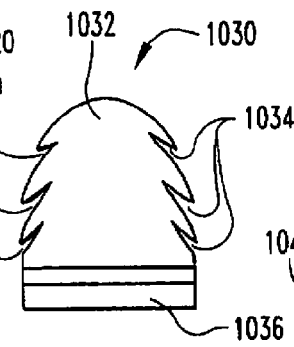 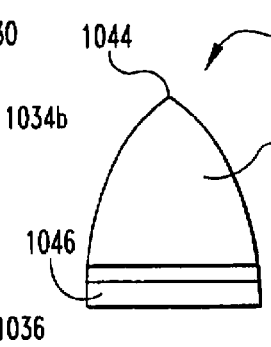 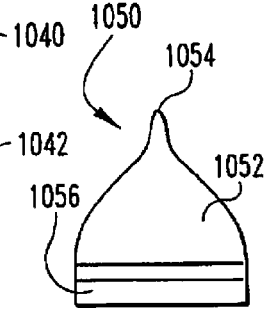
Fig. 3C  Fig. 3D  Fig. 3E  Fig. 3F
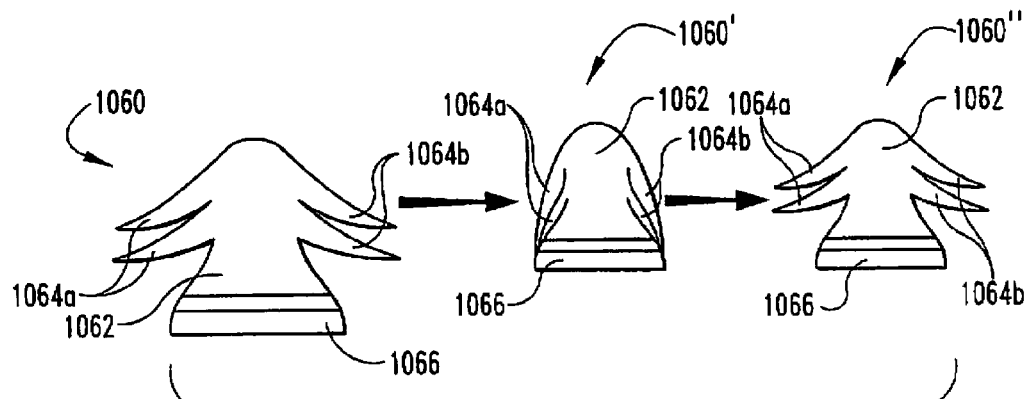
Fig. 3G

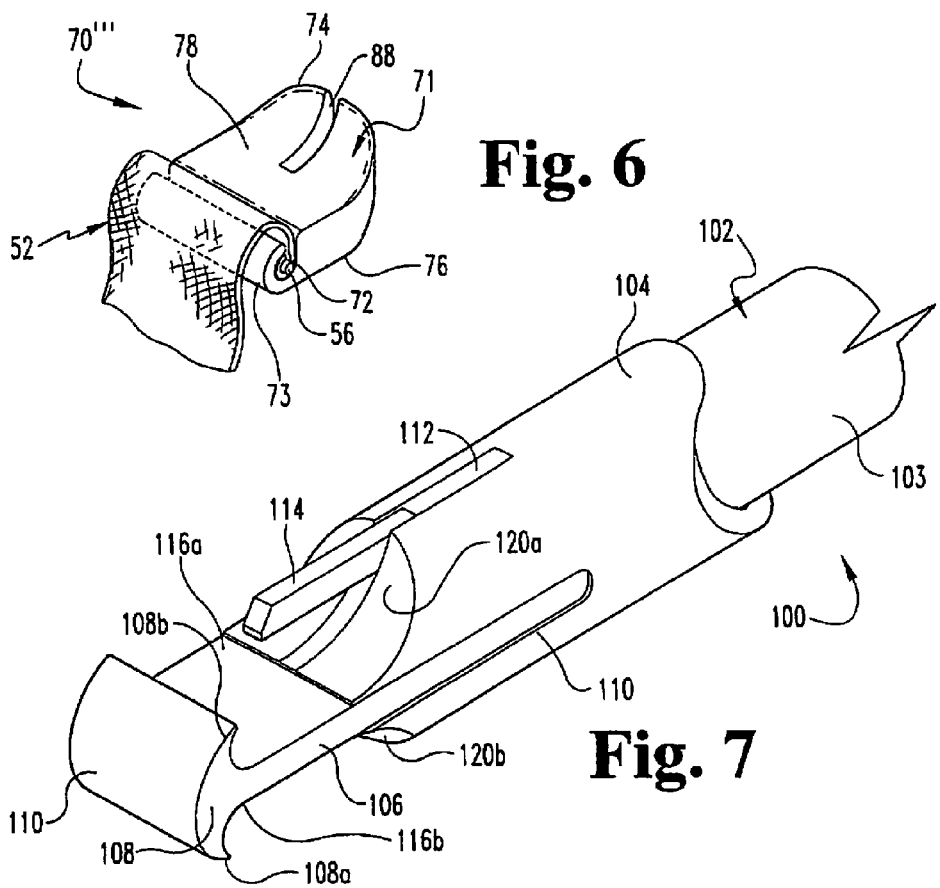
Fig. 6
Fig. 7
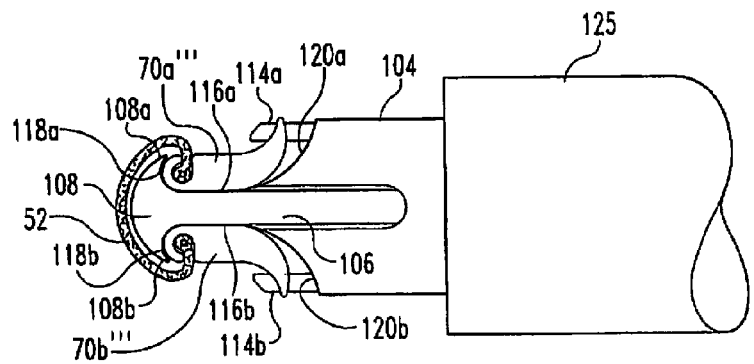
Fig. 8

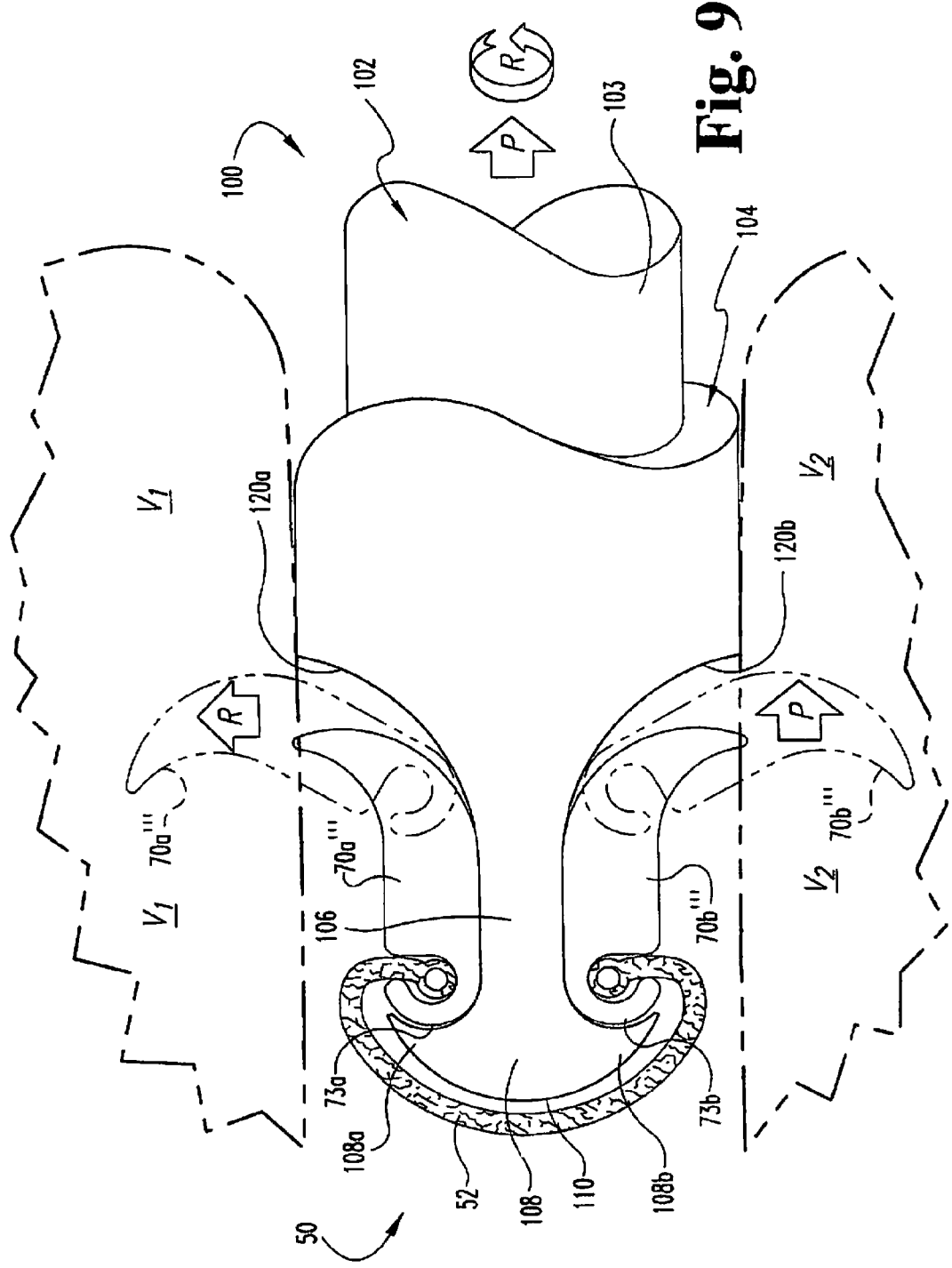

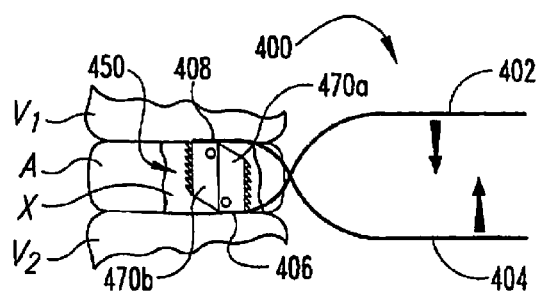
Fig. 18A
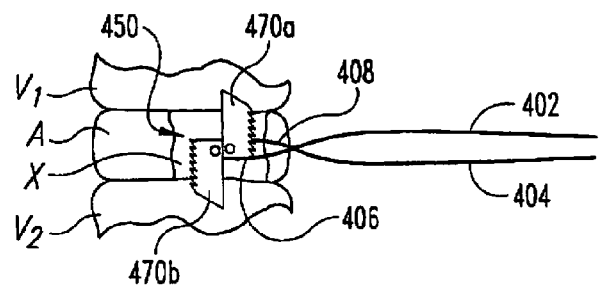
Fig. 18B
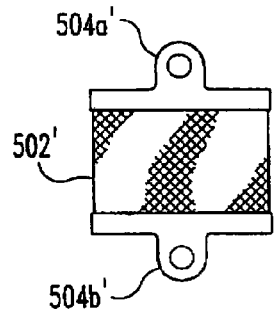 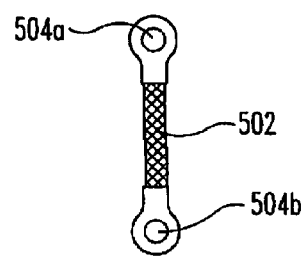 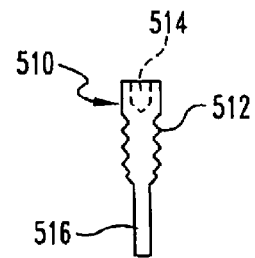
Fig. 19B    Fig. 19A    Fig. 19C
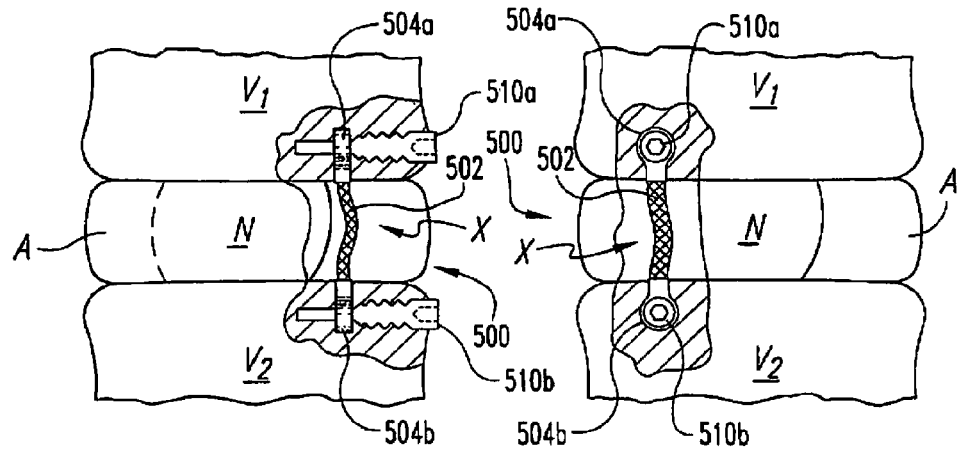
Fig. 20A    Fig. 20B

ANNULUS REPAIR SYSTEMS AND TECHNIQUES

CROSS-REFERENCE TO RELATED APPLICATIONS

The present application is a divisional of U.S. patent application Ser. No. 11/731,334, filed on Mar. 30, 2007, which is a continuation of application Ser. No. 10/123,367, filed on Apr. 16, 2002, issued as U.S. Pat. No. 7,223,289. Each of the referenced applications being incorporated by reference herein in their respective entirety.

BACKGROUND

The present invention relates generally to the field of spinal surgery, and more particularly to systems and techniques for repairing the annulus fibrosis of a spinal disc.

There are various surgical procedures and conditions that create a defect in the annulus fibrosis, such as, for example, an annulotomy, a discectomy, nucleotomy, implantation of artificial disc nucleus or artificial disc prosthesis, or repair of a disc herniation. Repair of annulus defects is normally perceived as time consuming and ineffective. Thus, annulus defects are commonly left unrepaired. This may lead to a higher incidence of disc reherniation or expulsion of the implant from the disc space.

In those procedures where the annulus is repaired via sutures that attempt to close the defect by pulling the surrounding tissue together, there are difficult challenges encountered. Often, the annulus defect is a relatively large hole that is difficult to close with conventional suturing techniques. It can also be difficult to actively engage the sutures in the surrounding annulus tissues, and the sutures could cut or tear through the annulus tissues after the repair has been made.

What is therefore needed are systems and methods for spinal surgery which provide an effective repair for defects in the annulus fibrosis. The present invention is directed toward meeting this need, among others.

SUMMARY

The present invention is directed to systems, techniques and methods for repairing annulus defects. Embodiments of the systems include at least one blocking member positionable in or adjacent to the annulus defect, one or more attachment portions coupled to the at least one blocking member for securing the blocking member to the adjacent vertebrae, and instruments for placing the blocking member in and/or adjacent to the annulus defect. The blocking member extends at least partially across the annulus defect for repair of the defect and/or retention of nucleus material, one or more implants, bio-compatible materials or devices, and/or other objects positioned in the disc space.

BRIEF DESCRIPTION OF THE DRAWINGS

FIG. 1 is an exploded perspective view directed to one embodiment of an annulus repair system.

FIGS. 2A-2C are side elevation views of various embodiments of anchors that can be employed with the annulus repair system of FIG. 1.

FIGS. 3A-3G are elevation views of various embodiments of anchors that can be employed with the annulus repair system of FIG. 1.

FIGS. 4A-4C illustrate a pre-insertion configuration and post-insertion configuration in section, and a post-insertion configuration in elevation, respectively, of the annulus repair system of FIG. 1 relative to a pair of adjacent vertebrae.

FIG. 5 illustrates a material stock from which a blocking member comprising part of an annulus repair system can be fabricated.

FIG. 6 illustrates a portion of an annulus repair system with another embodiment attachment portion.

FIG. 7 is a perspective view of a distal end portion of one embodiment instrument for inserting and engaging the annulus repair systems of the present invention, in an annulus defect.

FIG. 8 is an elevation view of the portion of the instrument of FIG. 7 with the annulus repair system of FIG. 6 mounted thereon and extending through a retractor sleeve.

FIG. 9 is an elevation view of the instrument and annulus repair system of FIG. 7 illustrating the insertion of the annulus repair system into the annulus defect and engagement of the annulus repair system to vertebrae adjacent the defect.

FIGS. 18A-18B illustrate schematically another embodiment instrument for inserting and engaging the annulus repair system of FIGS. 17A-17C to the vertebrae adjacent the annulus defect.

FIGS. 19A-19C are elevation views of another embodiment blocking member members and an anchor of an annulus repair system.

FIGS. 20A-20B are a side view and elevation view, respectively, in partial section of the blocking member and anchor of FIGS. 19A-19B engaged in an annulus defect.

DESCRIPTION OF THE ILLUSTRATED EMBODIMENTS

Figure 2D:
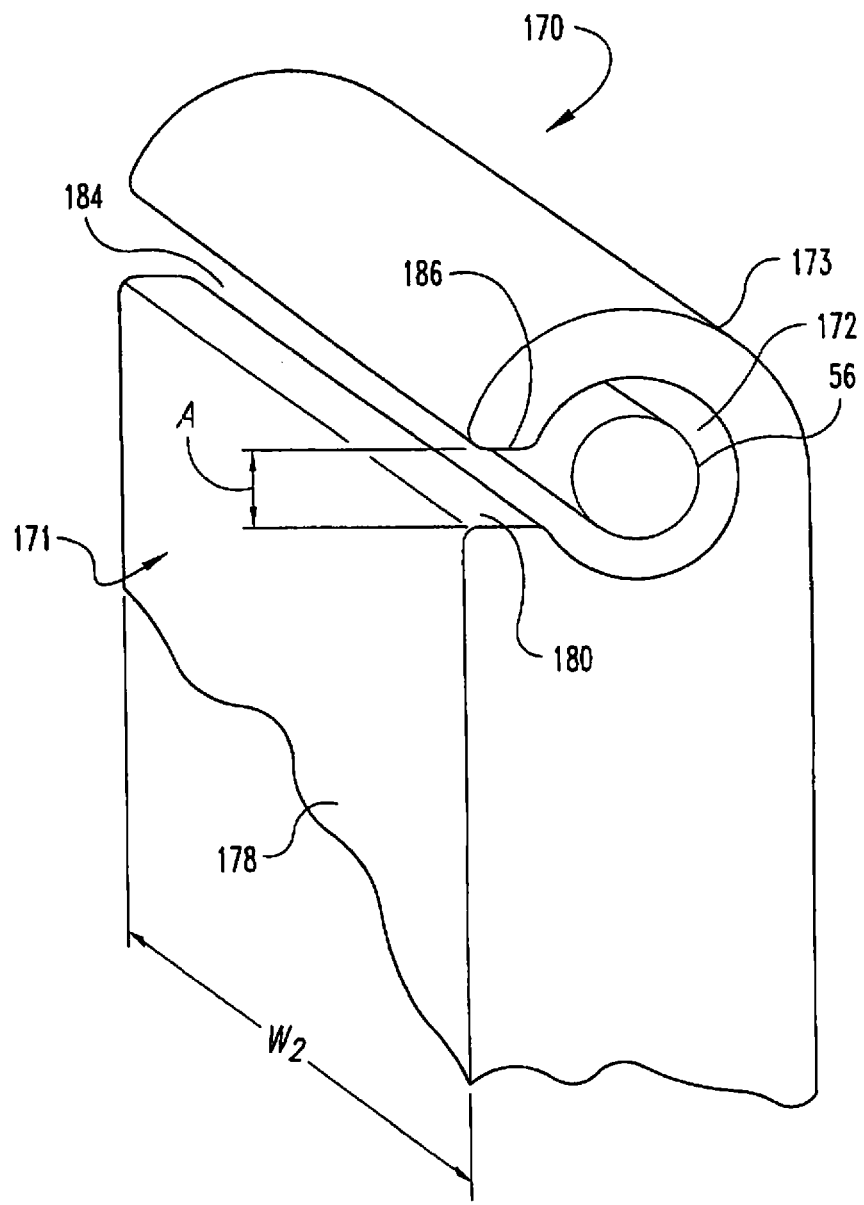
FIG. 2D is a perspective view of a portion of another embodiment anchor.

For the purposes of promoting an understanding of the principles of the invention, reference will now be made to embodiments illustrated in the drawings and specific language will be used to describe the same. It will nevertheless be understood that no limitation of the scope of the invention is thereby intended. Any such alterations and further modifications in the illustrated embodiments, and any such further applications of the principles of the invention as illustrated herein are contemplated as would normally occur to one skilled in the art to which the invention relates.

The annulus repair system and methods include a blocking member retained by one or more attachment portions within or adjacent a defect in the annulus fibrosis of a spinal disc. The blocking member can block all or a portion of the defect or void within the annulus fibrosis, such as may be caused by surgery or disc herniation. The one or more attachment portions can be connectable to or integrally formed with the blocking member. The attachment portions may be engaged to soft tissue and/or hard tissue or bone adjacent to the defect or void. Thus, the attachment portions retain the blocking member in a substantially fixed position within the defect or void relative to adjacent soft or hard tissue.

With respect to the various embodiments described herein, the attachment portion can be joined or fixed to the blocking member using various devices and/or techniques, or can be integrally formed with or an extension of the blocking member. The blocking member can be joined or attached to the attachment portion by, for example, sewing the attachment portion to the blocking member, thermal welding or bonding, adhesive bonding, three dimensional weaving or braiding, screws, staples, pins, tacks or rivet fixation. Furthermore, the attachment portion can be secured to the blocking member either before or after the blocking member is placed into or adjacent to the annulus defect.

The blocking member can be fabricated from components that are flexible or exhibit at least some flexibility. Examples of such components include woven fabric tubing, woven and non-woven mesh, or braided or woven structures, sutures, tethers, cords, planar members, bands, wires, cables, or any other component capable of extending across an annulus defect. Additionally, the blocking member may be resilient and/or elastic so it can assume various shapes during and after insertion and attachment. Growth factors or cells can be incorporated into the blocking member to accelerate the annulus repair process. Growth factors can be transforming growth factor β1, insulin-like growth factor 1, platelet-derived growth factor, fibroblast growth factor, bone morphogenetic protein (BMP), LIM mineralization protein (LMP) and combinations thereof.

The blocking member can be made from any biocompatible material, material of synthetic or natural origin, and material of a resorbable or non-resorbable nature. Suitable examples of blocking member material include autograft, allograft or xenograft; tissue materials including soft tissues, connective tissues, demineralized bone matrix and combinations thereof; resorbable materials including polylactide, polyglycolide, tyrosine-derived polycarbonate, polyanhydride, polyorthoester, polyphosphazene, calcium phosphate, hydroxyapatite, bioactive glass, collagen, albumin, fibrinogen and combinations thereof; and non-resorbable materials including polyethylene, polyester, polyvinyl alcohol, polyacrylonitrile, polyamide, polytetrafluorethylene, poly-paraphenylene terephthalamide, cellulose, and combinations thereof.

The attachment portion described herein can include anchors made from any biocompatible material, including synthetic or natural autograft, allograft or xenograft tissues, and can be resorbable or non-resorbable nature. Examples of tissue materials include hard tissues, connective tissues, demineralized bone matrix and combinations thereof. Further examples of resorbable materials are polylactide, polyglycolide, tyrosine-derived polycarbonate, polyanhydride, polyorthoester, polyphosphazene, calcium phosphate, hydroxyapatite, bioactive glass, and combinations thereof. Further examples of non-resorbable materials are carbon-reinforced polymer composites, shape-memory alloys, titanium, titanium alloys, cobalt chrome alloys, stainless steel, and combinations thereof.

Referring now to FIG. 1 there is illustrated annulus repair system 50 according to one embodiment of the present invention. The annulus repair system 50 includes a blocking member and an attachment portion for engaging the blocking member to one or more vertebrae adjacent the annulus defect. In the illustrated embodiment, repair system 50 includes a pair of anchors 70a, 70b and a blocking member 52 extending between anchors 70a, 70b. Blocking member 52 has a first end 54a and a second end 54b. First end 54a has a passage therethrough receiving coupling pin 56a, and second end 54b has a passage therethrough receiving coupling pin 56b.

Referring now further to FIG. 2A, anchors 70a and 70b, designated generally as anchor 70, each include a body 71 with a concave-convex curvature or spoon shape. First surface 76 has a convexly curved portion extending from tip 74 and a linear portion extending therefrom to end 73. Second surface 78 has a concave portion extending from tip 74 and a linear portion extending therefrom to end 73. End 73 includes a hook member 86 defining a receptacle 72 extending therealong between the sides of body 71. Receptacle 72 is sized to receive one of the ends 54a, 54b of blocking member 52 through opening 84 between hook member 86 and body 71. Receptacle 72 is also sized to receive a respective one of the coupling pins 56*a*, 56*b* laterally through the sidewall opening of receptacle 72; however, coupling pin 56*a* cannot pass through opening 84. Anchor 70 is coupled to blocking member 52 with a respective one of the coupling pins 56*a*, 56*b* in the passage of a respective end 54*a*, 54*b* of blocking member 52 with the end 54*a*, 54*b* positioned in receptacle 72.

In FIG. 2B there is shown another embodiment anchor 70' that is similar to anchor 70 discussed above. Anchor 70' includes a roughened portion 75 along convexly curved first surface 76 to resist anchor pullout from the vertebral body when inserted therein. Roughened portion 75 can include one or more teeth, spikes, serrations, knurlings, or barbs, for example, to engage the bony tissue. In FIG. 2C anchor 70" includes a roughened portion along concavely curved second surface 78. Other embodiments contemplated an anchor that includes a roughened portion along first surface 76 and second surface 78.

Referring now to FIG. 2D, there is shown another embodiment anchor 170 that is generally the same as anchor 70, but having an alternate end arrangement for connection with blocking member 52. Anchor 170 includes a body 171 having an end 173 defining a receptacle 172 for receiving pin 56 and an end 54*a*, 54*b* of the blocking member as discussed above with respect to anchor 70. An opening 184 is defined between hook member 186 and end surface 180 of body 171. Opening 184 has a width A sized to allow passage of blocking member 52 therethrough but preventing coupling pin 56 from being passed therethrough. End surface 180 is offset toward end 173 so that the end of hook member 186 and opening 184 is positioned more proximate end 173. This results in less length of blocking member 52 wrapped around hook member 186. Other embodiments contemplate that opening 184 can be positioned further toward end 173, including positioning of opening 184 between surfaces 176 and 178. Anchors 70, 170 can each be provided with a width W2 that is about the same as or greater than width W1 of the blocking member to which it is coupled.

FIGS. 3A-3G provide further embodiment anchors having a shape similar to that of anchor 70 and connectable to a blocking member. In FIG. 3A anchor 1000 includes a body 1002 having an end 1006 for engagement with a blocking member and a hole 1004 formed through body 1002. In FIG. 3B anchor 1010 includes a body 1012 having an end 1016 for engagement with a blocking member. Body 1012 includes a first hole 1014*a* and a second hole 1014*b* formed therethrough. Hole 1004 in anchor 1000 and holes 1014*a*, 1014*b* of anchor 1010 provide avenues for bone ingrowth through the anchor for long term fixation in the vertebral bodies. The holes can also receive fasteners to engage the anchor to the vertebral body.

In FIG. 3C there is an anchor 1020 including a body 1022 having an end 1026 for engagement with a blocking member. Body 1022 also includes a first cutout 1024*a* in one side thereof and a second cutout 1024*b* in the opposite side thereof. In FIG. 3D anchor 1030 includes a body 1032 having an end 1036 for engagement with a blocking member. Body 1032 includes a number of first cutouts 1034*a* in one side thereof and a number of second cutouts 1034*b* in the opposite thereof. In the illustrated embodiment, three cutouts 1034*a*, 1034*b* are provided. Cutouts 1034 are relatively smaller than cutouts 1024 so that an increased number of cutouts can be provided while maintaining the structural integrity of anchor 1030. The cutouts of anchors 1020, 1030 provide initial fixation by providing barbs or pointed surfaces facing away from the insertion direction along the edges of the anchor that resist anchor pullout from the vertebral body. Long term fixation of anchors 1020, 1030 is enhanced by bone growth through the cutouts.

In FIG. 3E there is an anchor 1040 that includes a body 1042 having an end 1046 for engagement with a blocking member. Body 1042 includes an ogival tip 1044 extending between the edges of body 1042 opposite end 1046 to facilitate penetration through the vertebral endplate and into the vertebral body. In FIG. 3F there is shown an anchor 1050 that includes a body 1052 having an end 1056 for engagement with a blocking member. Body 1052 includes a pointed end 1054 opposite end 1056 to facilitate penetration through the vertebral endplate and into the vertebral body.

In FIG. 3G there is an anchor 1060 having a body 1062 with an end 1066 for engagement with a blocking member. Body 1062 includes a number of flexible first member 1064*a* along one side thereof and a number of flexible second members 1064*b* along the opposite side thereof. Members 1064*a*, 1064*b* are normally flexed away from body 1062 and extend away from the insertion direction, as shown by anchor 1060. During insertion into the vertebral body, members 1064*a*, 1064*b* flex inwardly along body 1062 to provide a substantially smooth edge profile along body 1062, as shown by anchor 1060', to facilitate insertion. After insertion, a pullout force exerted on body 1062 causes members 1064*a*, 1064*b* to flex away from body 1062 and engage the bony tissue, as shown by anchor 1060".

The annulus repair systems are positionable in or adjacent an annulus defect X between vertebrae V1 and V2, such as shown in FIGS. 4A-4C, for repair or reconstruction of annulus A. It is contemplated that defect X in annulus A may have been created in order to perform an annulotomy, discectomy, nucleotomy or some other procedure in the disc space, and/or defect X has resulted due to aging, trauma, degenerative condition, or the like. It is further contemplated that the nucleus N of the spinal disc can be the natural spinal disc nucleus pulposus, or can be an artificial disc nucleus or disc prosthesis, fusion device or some other device that has been inserted into the disc space through defect X. The remaining portion of annulus A extending around the nucleus is substantially intact, or has been repaired using the system and method of the present invention or some other known annulus repair technique.

Annulus repair system 50 is shown in FIG. 4A with blocking member 52 positioned in or adjacent to annulus defect X, anchor 70*a* extending along the endplate of vertebra V1, and anchor 70*b* extending along the endplate of vertebra V2. Blocking member 52 can be made from flexible material and collapsed, folded or otherwise positioned in a reduced size configuration for insertion into or adjacent to defect X. In FIG. 4B anchors 70*a*, 70*b* have been moved from their FIG. 4A position and are embedded in a respective one of the vertebral bodies V1, V2 through the cortical rim or vertebral endplate. It is contemplated that blocking member 52 has a length between anchors 70*a*, 70*b* sufficient to extend along height H of defect X between anchors 70*a*, 70*b*. It should be understood that it is contemplated that the other embodiment anchors can also be employed with repair system 50 and embedded in vertebrae V1 and V2

As shown in FIG. 4C, width W1 of blocking member 52 along annulus A can be about the same as or less than width W of defect X so that blocking member 52 extends across all or a portion of defect X, thereby effectively blocking defect X and implants or disc material in the disc space from protruding or expelling through defect X, as indicated by arrow F in FIG. 4B. In one embodiment, width W1 of blocking member 52 is about 90% or less than width W of defect X. In another embodiment, width W1 of blocking member 52 is about 50% or less than width W of defect X. In a further embodiment, width W1 of blocking member 52 is about 10% or less than width W of defect X. In addition, blocking member 52 can have a depth D1 that is less than the depth D of annulus A at defect X, providing additional unobstructed or unoccupied area in defect X for growth and regeneration of annulus tissue.

It is also contemplated that blocking member 52 can be provided with width W1 that is greater than width W of defect X. In such an embodiment, width W of the annulus defect X can be dilated to accommodate width W1 of blocking member 52 for insertion into the defect. As the annulus tissue returns to its pre-dilated state, the surrounding annulus tissue will press against the width of blocking member 52. Alternatively, blocking member 52 is positioned along the exterior surface of the disc space and overlaps the exterior of the annulus tissue for attachment thereto and/or the adjacent vertebral bodies. It is contemplated in such embodiments that width W1 can be up to 50% greater than width W of defect X.

It is contemplated that anchors 70a, 70b engage vertebrae V1 and V2 with sufficient pullout resistance that supplemental fixation is not required. However, supplemental fixation can also be provided to further increase pullout resistance of anchors 70a, 70b. Fasteners 80a, 80b can be engaged to anchors 70a, 70b in the respective vertebrae V1 and V2 to provide increased pullout resistance, as shown in FIGS. 4B and 4C. A hole is drilled and/or tapped in each vertebra and through the respective anchor 70a, 70b. Fastener 80a is placed in the hole in vertebra V1 through anchor 70a, and fastener 80b is placed in the hole in vertebra V2 through anchor 70b. Anchors 70a, 70b can also be provided with holes preformed therethrough for receipt of fasteners 80a, 80b. Fasteners 80a, 80b can have a threaded distal end portion as shown, or can have a threaded proximal portion with a pin extending distally from the threaded proximal portion for positioning through holes in anchors 70a, 70b.

In FIG. 5 there is shown one embodiment of a material stock from which blocking member 52 can be fabricated. Stock material 90 has a tubular form and sized to provide a number of blocking members 52a, 52b, 52c, and 52d. Trim areas 96 are provided between adjacent blocking members to allow width W1 of the blocking member to be sized as desired. Stock material 90 can be provided with a basic underlying webbing structure 94 around which reinforcement webbing 92 is provided. Underlying webbing structure 94 can be adhered to or interwoven with a backing 98 that extends along the length of stock material 90. In the illustrated embodiment, the underlying webbing structure 94 includes vertical fibers and horizontal fibers, while the reinforcement webbing 92 includes diagonal fibers. The different fiber orientations provide resistance to extension, lateral bending and rotational loading applied to blocking member 52 by movement of the spinal column at defect X.

In FIG. 6 there is shown another embodiment anchor 70''' attached to blocking member 52. Anchor 70''' is similar to anchor 70, but includes a notch 88 extending from tip 74 and into body 71. As discussed further below, notch 88 is sized to receive a retaining member to to couple anchor 70''' to an insertion instrument.

Referring now to FIG. 7 there is shown one embodiment of an insertion instrument 100 for inserting and engaging repair system 50 in an annulus defect. Instrument 100 includes a mounting member 102 movably positioned in an actuating member 104. Mounting member 102 includes a distal mounting portion 106 having a driving member 108 at a distal end thereof. Driving member 108 includes an upper driving portion 108a and a lower driving portion 108b. Each of the driving portions 108a, 108b include a proximally oriented driving surface 118a, 118b, respectively. Mounting portion 106 further includes an upper mounting surface 116a extending from upper driving portion 108a, and a lower mounting surface 116b extending from lower driving portion 108b. Upper mounting surface 116a and lower mounting surface 116b extend generally parallel to one another and into actuating member 104. The side surfaces between upper mounting surface 116a and lower mounting surface 116b can be convexly curved between surfaces 116a, 116b or otherwise shaped to provide a caroming action to drive the anchors into the adjacent vertebral bodies upon rotation of mounting portion 106, as discussed further below.

Actuating member 104 includes an upper actuating surface 120a and a lower actuating surface 120b at a distal end thereof. Actuating surfaces 120a, 120b are concavely shaped to engage the attachment portion, such as convexly curved first surface 76 of anchor 70''' or the other anchors described herein. Actuating member 104 further includes an upper retainer 114a and a lower retainer 114b extending distally therefrom in slots 112 (only one shown in FIG. 7.) Upper and lower retainers 114a, 114b are moveable relative to actuating member 104 to selectively engage and disengage an anchor on mounting portion 106, such as notch 88 in anchor 70'''.

As shown in FIGS. 8 and 9, annulus repair system 50 having attachment portions with anchors 70a', 70b' is mounted on mounting portion 106. Driving surface 118a of upper driving portion 108a is in contact with end 73a of upper anchor 70a', and driving surface 118b of lower driving portion 108b is in contact with the end 73b of anchor 70b'. The body of anchor 70a' is position on upper mounting surface 116a with the concave side of the anchor oriented toward the endplate of the upper vertebra V1. The body of anchor 70b' is positioned on lower mounting surface 116b with the concave side of the anchor oriented toward the endplate of the lower vertebra V2. Blocking member 52 extends around the distal end of driving member 108 between anchor 70a' and anchor 70b'. The distal end 110 of driving member 108 can have a convex profile extending between upper driving portion 108a and lower driving portion 108b to maintain blocking member 52 in a taut or relatively taut condition as it is inserted.

Upper and lower retainers 114a, 114b are positionable in respective ones of the notches 88 of anchor 70a', 70b' to maintain repair system 50 on mounting portion 106 before and during insertion to defect X. When repair system 50 is in a desired insertion position relative to defect X, the upper and lower retainers 114a, 114b can be withdrawn from notches 88 by a tool or another actuating portion (not shown) associated with insertion instrument 100. It is contemplated that mounting portion 106 can be detachable from a proximal shaft 103 of mounting member 102. Shaft 103 and actuating member 104 can be provided as a re-useable instrument, with repair system 50 and mounting portion 106 provided as a disposable cartridge attachable to proximal shaft portion 103. In this form, a number of mounting portions 106 can be provided with variously sized repair systems 50 pre-mounted thereon, and the surgeon can select the repair system providing a blocking member of desired height and width.

Insertion of repair system 50 to defect X with insertion instrument 100 can be performed through an open incision with tissue retracted to expose annulus defect X, through a micro-incision, or through a retractor sleeve such as sleeve 125 shown partially in FIG. 8. In FIG. 9, repair system 50 is positioned in defect X with insertion instrument 100. Mounting member 102 is moved proximally in the direction of arrow P to bring anchors 70a', 70b' into contact with respective ones of the actuating surfaces 120a, 120b. As mounting member 102 is moved further in the direction P, actuating surfaces 120a, 120b drive respective ones of the anchors 70a', 70b' to a first actuated position into the endplate of the adjacent vertebra V1, V2. When driving member 108 is adjacent actuating surfaces 120a, 120b then anchors 70a', 70b' cannot be further driven into the endplates by proximal movement P. Anchors 70a', 70b' can be further driven into the endplates to a second actuated position by rotating insertion instrument 100 in either rotational direction, such as that indicated by arrow R. Rotation of insertion instrument 100 causes mounting portion 106 to act as a camming member that further drives anchors 70a, 70b into the respective endplates of vertebrae V1 and V2.

Figure 10A:
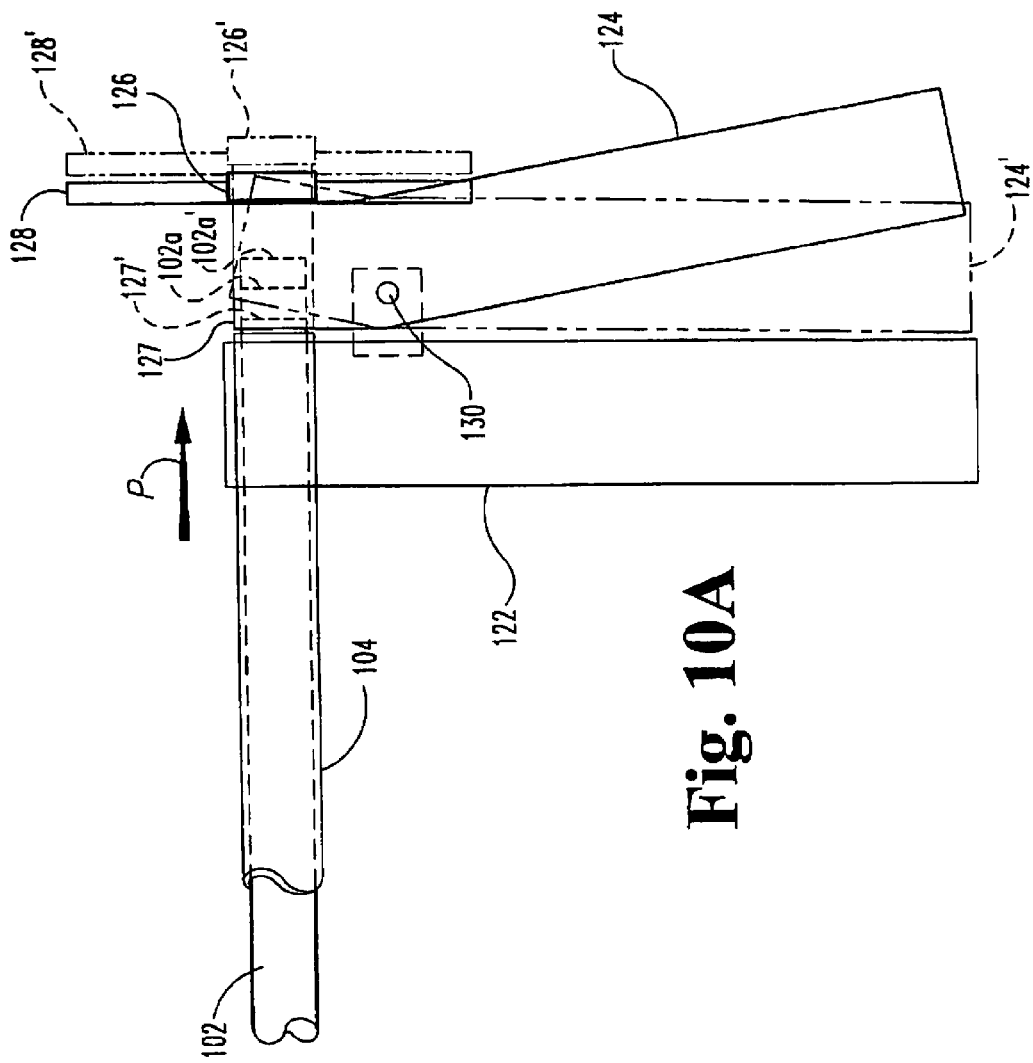
FIGS. 10A-B illustrate an elevation view and end view, respectively, of one embodiment proximal portion for the instrument of FIG. 7.
Figure 10B:
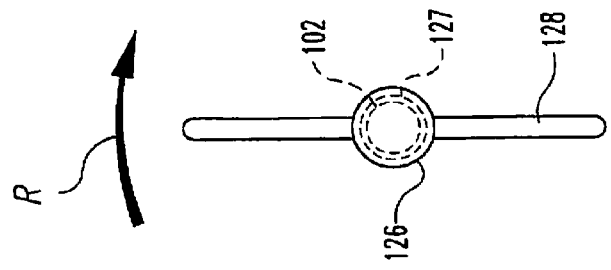

Referring now to FIGS. 10A and 10B, there is shown one embodiment of a handle system that can comprise a proximal portion of insertion instrument 100. The handle system includes a fixed arm 122 and a movable arm 124 pivotally coupled thereto. Actuating member 104 is secured to fixed handle 122. The handle system further includes an end member 126 and a cylinder 127 extending around a distal portion of mounting member 102 and threadingly engaged thereto. A torque arm 128 extends outwardly from end member 126. Movable arm 124', end member 126' and torque arm 128' are shown in dashed lines in the unactuated state of annulus repair system 50. Torque arm 128 can be provided in the form of a pin, rod or other member that can be grasped by the surgeon to rotate end member 126 and cylinder 127 as indicated by arrow R (or in the direction opposite arrow R). This in turn moves mounting member 102 linearly and proximally with respect to actuating member 104, and the anchors are driven or cammed along actuating surfaces 120a, 120b to penetrate the vertebral endplates.

Mounting member 102 is driven proximally in the direction of arrow P to actuate the anchors of repair system 50 mounted thereon with actuating surface 120a, 120b, as indicated by the movement of proximal end 102a of mounting member 102 to the location indicated by proximal end 102a'. In this actuated position, the upper end of movable arm 124 is positionable against or adjacent fixed arm 122 by pivoting the moveable arm 124 about pivot pin 130 to the position indicated in solid lines. This indicates to the surgeon that initial actuation is complete. Movable handle 124 can also block torque arm 128 from further rotation by contact of torque arm 128 with handle 124 and/or by contact between fixed handle 122 and movable handle 124 at the upper ends thereof. The entire handle assembly can then be rotated in the direction of arrow R (or in the direction opposite arrow R) to rotate mounting member 102, causing the camming surfaces along and/between mounting surfaces 116a, 116b of mounting portion 106 to further drive the anchors of repair system 50 into the adjacent vertebrae.

In one specific embodiment, it is contemplated that the proximal portion of actuating member 104 is a 10 millimeter diameter tube mounted to fixed arm 122, and the proximal portion 103 of mounting member 102 is an 8 millimeter diameter rod mounted to moveable arm 124. Insertion instrument 100 can have a length extending between the distal end of mounting member 102 and the inside of fixed arm 122 of about 7 inches. The pullback of mounting member 102 relative to actuating member 104 for actuating repair system 50 from its insertion configuration to a first actuated position can be about 3 millimeters, and thereafter torque applied to cam the anchors of repair system 50 to a second actuated position where the anchors are further embedded in the adjacent vertebrae.

Figure 11:
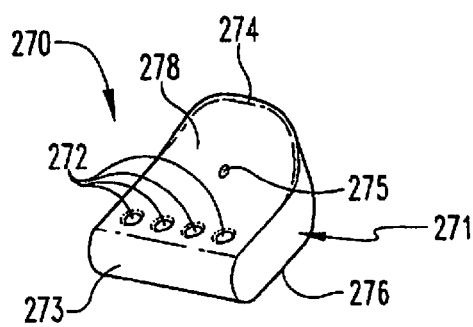
FIG. 11 is a perspective view of another embodiment anchor.

Referring now to FIG. 11, there is shown another embodiment anchor 270 to which a blocking member can be engaged before insertion or after insertion of the anchor 270 into the vertebral endplate. Anchor 270 includes a body 271 having an edge 274 at one end thereof for insertion into the vertebral endplate. Body 271 further includes a first surface 276 having a convex portion and an opposite second surface 278 having a concave portion. A number of holes 272 are formed through body 271 between first surface 276 and second surface 278 adjacent end 273. An end of a blocking member can be attached to anchor 270 with sutures, rivets, screws or other fasteners that extending through the blocking member and into or through holes 272.

Figure 12A:
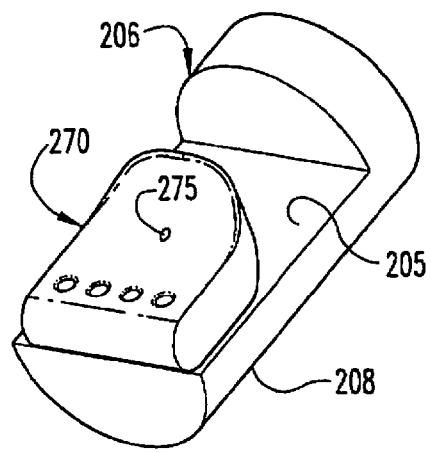
FIGS. 12A-12C are a perspective view, elevation view, and end view, respectively, of the anchor of FIG. 11 mounted to an insertion instrument.
Figure 12B:
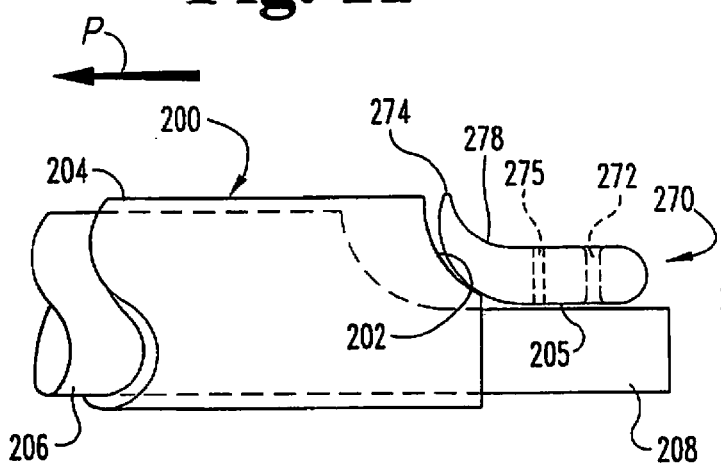
Figure 12C:
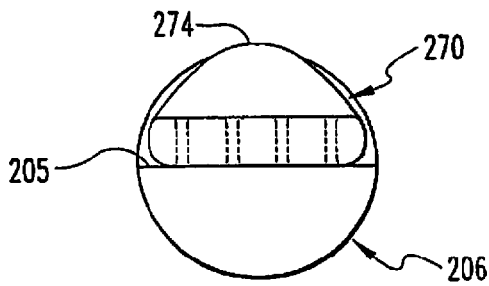

As shown in FIGS. 12A to 12C, anchor 270 can be mounted on mounting member 206 of insertion instrument 200. Mounting member 206 includes a mounting portion 208 having a mounting surface 205 upon which anchor 270 is positioned. Anchor 270 includes a hole 275 through which a fastener can extend to provisionally engage anchor 279 to mounting portion 208. Insertion instrument 200 includes an actuating member 204 in which mounting member 200 is movably positioned. Mounting member 204 includes an actuating surface 202 at a distal end thereof. As mounting member 206 is moved in the direction of arrow P relative to actuating member 204, actuating surface 202 contacts first side 276 of anchor 270, moving tip 274 away from mounting portion 206 and into the adjacent vertebral endplate.

Figure 13:
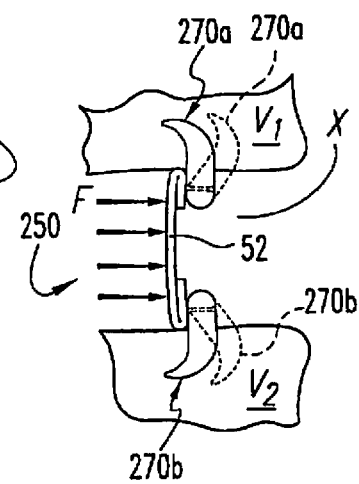
FIG. 13 illustrates the anchors of FIG. 11 engaged in an annulus defect to the adjacent vertebrae with a blocking member extending therebetween.

As shown in FIG. 13, blocking member 52 can be secured to the inserted anchors 270a, 270b to provide repair system 250. It is contemplated that blocking member 52 can be attached to respective ones of the anchors 270a, 270b after one or both of the anchors are engaged to the adjacent vertebral endplates. It is further contemplated that blocking member 52 can be pre-attached to anchors 270a, 270b and inserted as discussed above with respect to insertion instrument 100. Once in position in defect X, blocking member 52 can resist expulsion or protrusion forces, indicated by arrows F, created by an implant or disc material.

Figure 14:
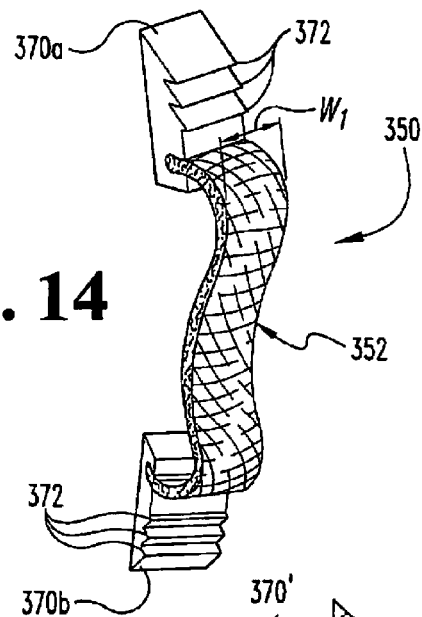
FIG. 14 is a perspective view of another embodiment annulus repair system.
Figure 15A:
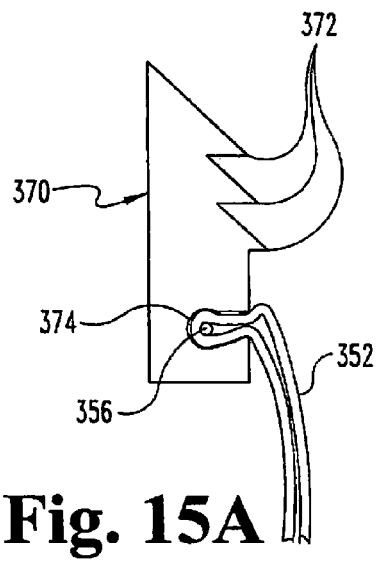
FIGS. 15A-15C illustrate various means for attaching a blocking member to an anchor.

Referring now to FIG. 14 there is shown another embodiment annulus repair system 350. Repair system 350 includes a blocking member 352 having an attachment portion including a first anchor 370a attached at one end thereof and a second anchor 370b attached to another end thereof. Blocking member 352 is similar to blocking member 52 discussed above. Blocking member 352 includes a width W1 that extends across all or a portion of width W of defect X. Anchor 370 includes a number of teeth, barbs, serrations or other engagement means 372 formed along one side thereof Referring now to FIGS. 15A to 15C, there is shown various means for connecting the blocking member to an attachment portion. In FIG. 15A anchor 370 includes a receptacle 374 extending along one end thereof. Blocking member 352 is in looped form and has one end in receptacle 374. In a manner similar to that discussed above with respect to anchor 70, a coupling pin 356 is positioned within a looped portion of blocking member 352 in receptacle 374 to retain the end of blocking member 352 therein.

Figure 15B:
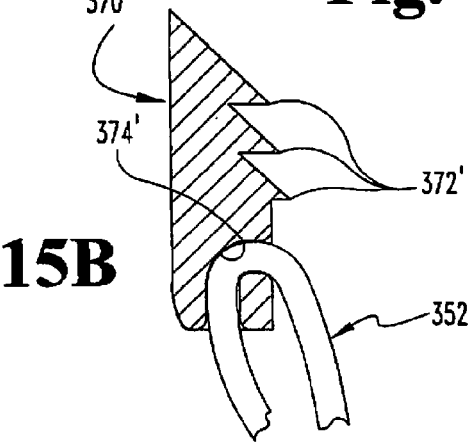
Figure 15C:
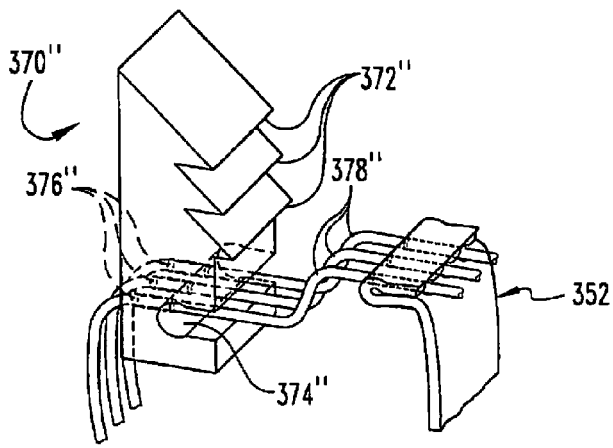

In FIG. 15B anchor 370' includes teeth 372' extending along one side thereof. Anchor 370 includes a passage 374' formed in one end thereof through which a looped portion of blocking member extends to couple anchor 370' thereto. In this embodiment, the width of blocking member 352 could be less than the width of the anchor 370' so that passage 374' is formed along a portion of the width of anchor 370'. In FIG. 15C, anchor 370" includes teeth 372" and a receptacle 374" along one end thereof. Anchor 370" further includes one or more holes 376" extending therethrough in communication with receptacle 374". Blocking member 352 can be attached to anchor 370" in receptacle 374" with sutures 378" extending through holes 376" and also through blocking member 352. In the illustrated embodiment, the end of blocking member 352 is folded upon itself in order to provide a reinforced area of material for sutures 378" to engage.

Figure 16A:
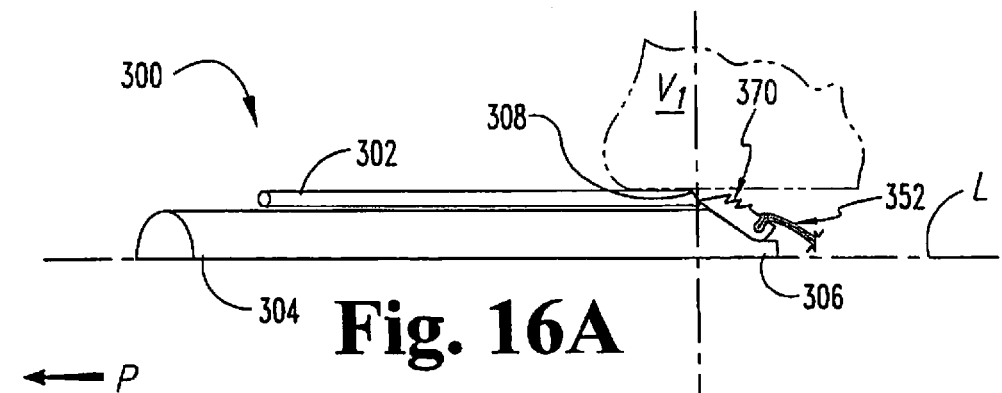
FIGS. 16A-16C are partial elevation views of a portion of an insertion instrument and annulus repair system of FIG. 14 illustrating the insertion and engagement of the annulus repair system at the annulus defect.
Figure 16B:
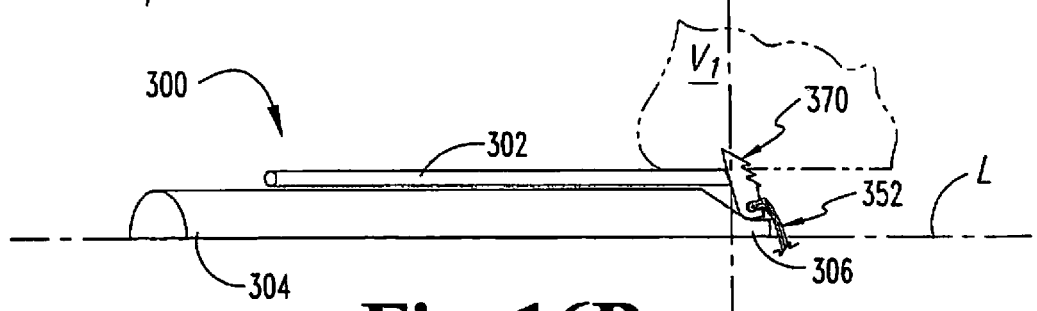
Figure 16C:
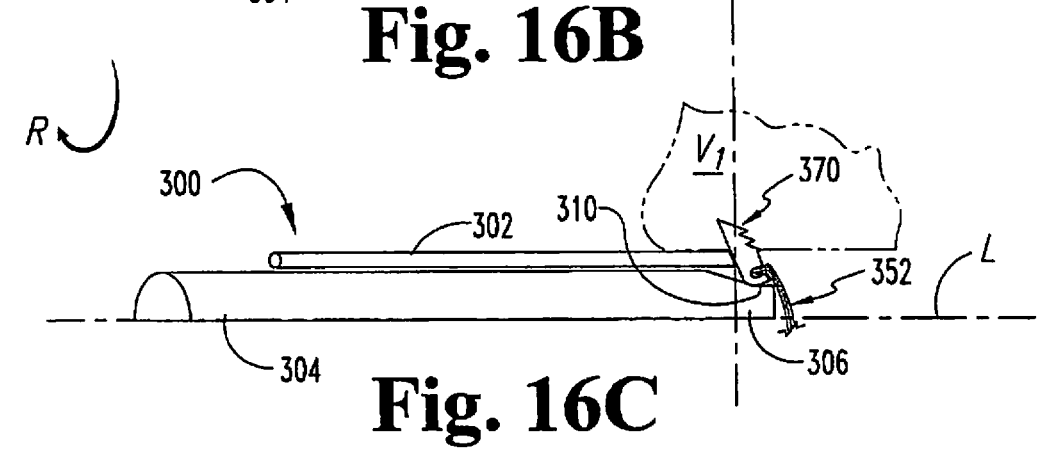

Referring now to FIGS. 16A-16C, there is shown another embodiment insertion instrument 300 for inserting the repair system of the present invention. Instrument 300 is described with reference to repair system 350, although application with other repair systems described herein is also contemplated. In FIGS. 16A to 16C, only the upper half of insertion instrument 300 is shown, it being understood that the lower half of insertion instrument 300 can be symmetrical thereto. Instrument 300 includes a mounting member 304 movably positioned along an actuating member 306. Anchor 370 is mounted to mounting member 304, such as described above with respect to insertion instruments 100 and 200. As mounting member 304 is pulled proximally in the direction of arrow P relative to actuating member 302 as shown in FIG. 16B, anchor 370 is pushed to a first actuated position into the endplate of vertebra V1 by actuating surface 308 of actuating member 302. When mounting member 304 has been actuated to the first actuated position relative to actuating member 302, mounting member 304 is rotated in the direction of arrow R. Camming surface 310 of mounting member 304 pushes against the end of anchor 370 to push anchor 370 to a second actuated position further embedded into the endplate of vertebra V1. Blocking member 352 can be engaged to anchor 370 before or after engagement of anchor 370 with the adjacent vertebra.

Figure 17A:
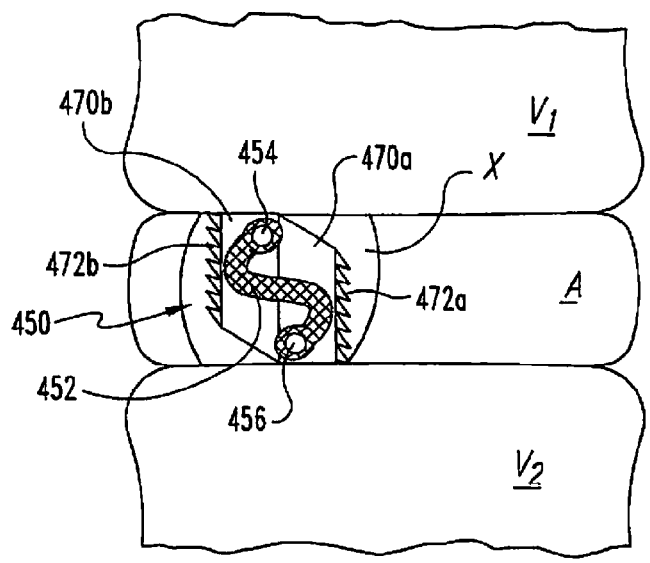
FIGS. 17A-17C illustrate another embodiment annulus repair system in an annulus defect in a pre-engagement configuration, in an engaged configuration, and in a plan view, respectively.
Figure 17B:
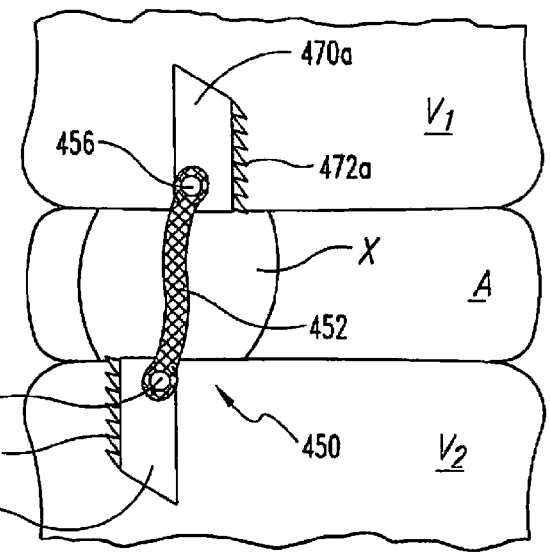
Figure 17C:
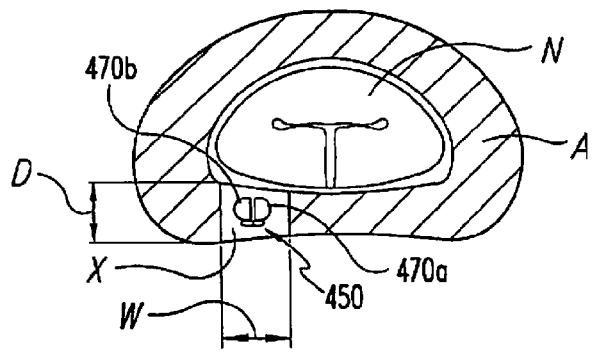

Referring now to FIGS. 17A to 17C, there is shown another embodiment annulus repair system 450. Repair system 450 includes a blocking member 452 and an attachment portion coupled to blocking member 452. The attachment portion includes a first anchor 470a coupled to one end of blocking member 452 and a second anchor 470b coupled to the other end of blocking member 452. In the illustrated embodiment, blocking member 452 is attached to anchor 470a with pin 454, and the other end of blocking member 452 is attached to anchor 470b with pin 456. This allows the end of blocking member 452 to rotate relative to the anchor as repair system 450 is moved from its insertion position to its actuated or engaged position. Other means for attaching blocking member 452 to anchors 470a, 470b are also contemplated.

In FIG. 17A repair system 450 is shown in its insertion position adjacent to or in defect X in annulus A between vertebrae V1 and V2. In FIG. 17B repair system 450 has been actuated or moved to an actuated position in which anchors 470a, 470b have been moved away from one another for engagement to vertebrae V1 and V2, respectively. Anchors 470a, 470b can be provided with teeth, barbs, serrations, spikes 472a, 472b or other means therealong to resist pullout from the vertebral body when inserted therein.

In FIG. 17C it is shown with repair system 450 and blocking member 452 that the blocking members described herein need not occupy the entire depth D of defect X, but rather only a portion thereof. However, it is also contemplated that the blocking members described herein could occupy all or a substantial portion of depth D. Furthermore, the blocking member can be centered laterally along width W and also along depth D to minimize the size of any unblocked area in defect X. However, repair system 450 could also be offset laterally to one side of defect X in order to, for example, provide room for a second repair system. Repair system 450 could also be positioned at various locations along depth D depending on operative and/or anatomical conditions encountered by the surgeon.

In FIGS. 18A and 18B, there is shown a schematic of an insertion instrument for actuating or moving repair system 450 from its insertion position in defect X to its engaged position with vertebrae V1 and V2. Insertion instrument 400 includes a first arm 402 coupled to a second arm 404. Anchor 470a is mounted on or in contact with a distal mounting portion 406 of first arm 402, and second anchor 470b is mounted on or in contact with distal mounting portion 408 of second arm 404. First arm 402 and second arm 404 can be moved relative to one another from an insertion configuration of FIG. 18A where anchors 470a, 470b are positioned in or adjacent to defect X to an actuated configuration in FIG. 18B where anchors 470a, 470b are engaged to vertebrae V1, V2, respectively. Blocking member 452 can be engaged to anchors 470a, 470b before or after engagement of anchors 470a, 470b with vertebra V1, V2.

Referring now to FIG. 19A, there is shown another embodiment blocking member 502. Blocking member 502 has a body formed of a suture, braid, cord, rope, or strand like material. First end 504a of blocking member 502 includes an attachment portion with an eyelet and second end 504b also includes an attachment portion with an eyelet. Another embodiment blocking member 502' is shown in FIG. 19B. Blocking member 502' has a body formed of a sheet of material that can be woven or non-woven material. First end 504a' of blocking member 502' includes an attachment portion with an eyelet and second end 504b' also includes an attachment portion with an eyelet. The ends of blocking members 502, 502' can be crimped, sewn, riveted, screwed, clamped, glued or otherwise fastened to the attachment portions. The attachment portion further includes an anchor 510 in the form of a pin fastener as shown in FIG. 19C. Anchor 510 has a threaded portion 512 and a pin 516 extending distally therefrom. A tool engaging recess 516 is provided at the proximal end of the pin fastener.

FIGS. 20A and 20B show a repair system 500 including blocking member 502 and an attachment portion including anchors 510a, 510b. Blocking member 502 is positioned in defect X with its first end 504a positioned in a tunnel or hole formed from the endplate of vertebra V1 into the body of vertebra V1. The second end 504b of blocking member 502 is positioned in a tunnel or hole formed from the endplate of vertebra V2 into the body of vertebra V2. Anchor 510a is positioned in a bore or hole extending from a face of vertebra V1 so that pin 516 extends through the eyelet at first end 504a. Anchor 510b is positioned in a bore or hole extending from a face of the vertebra V2 so that pin 516b extends through the eyelet at second end 504b.

It is contemplated that the face of vertebrae V1 and V2 from which anchors of the repair systems described herein could extend include the anterior, antero-lateral, lateral, posterior-lateral or posterior portion of vertebrae V1, V2. It should also be understood that blocking member 502' could similarly be secured in defect X, and that blocking member 502' can be provided with a width as discussed above with respect to blocking member 52.

Figure 21A:
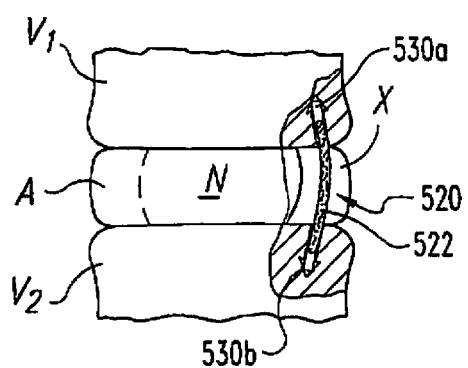
FIGS. 21A-21B are a side view and elevation view, respectively, in partial section of another embodiment annulus repair system engaged in an annulus defect.
Figure 21B:
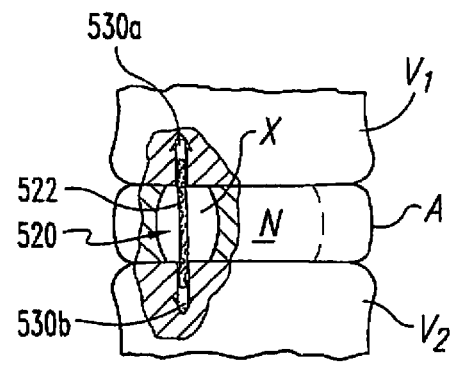

FIGS. 21A and 21B show a repair system 520 including blocking member 522 and an attachment portion including anchors 530a, 530b. In order to attach blocking member 522 to vertebrae V1 and V2, blocking member 522 is positioned in defect X with its upper end positioned in a tunnel or hole formed from the endplate of vertebra V1 into the body of vertebra V1. The lower end of blocking member 522 is positioned in a tunnel or hole formed from the endplate of vertebra V2 into the body of vertebra V2. Anchor 530a is attached to the upper end of blocking member 522 with a suture or the like and extends in the same tunnel or hole as the upper end of blocking member 522. Anchor 530b is attached to the lower end of blocking member 522 with a suture or the like and extends in the same tunnel or hole as the lower end of blocking member 522. In the illustrated embodiment, anchors 530a, 530b include pivotal gulls extending therefrom to resist pullout from the vertebral body in which the anchor is engaged.

Figure 22A:
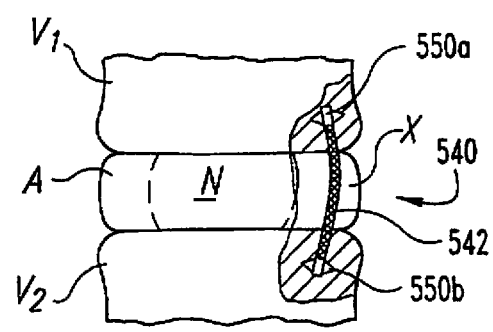
FIGS. 22A-22B are a side view and elevation view, respectively, in partial section of another embodiment annulus repair system engaged in an annulus defect.
Figure 22B:
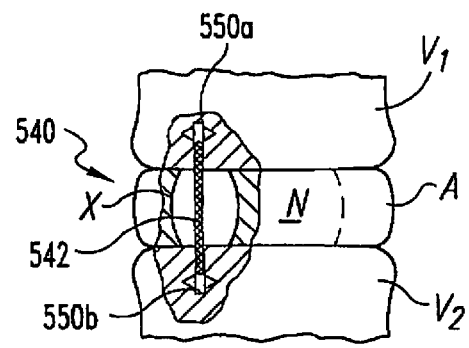

FIGS. 22A and 22B show a repair system 540 including blocking member 542 and an attachment portion including anchors 550a, 550b. In order to attach blocking member 542 to vertebrae V1 and V2, blocking member 542 is positioned in defect X with its upper end positioned in a tunnel or hole formed from the endplate of vertebra V1 into the body of vertebra V1. The lower end of blocking member 542 is positioned in a tunnel or hole formed from the endplate of vertebra V2 into the body of vertebra V2. Anchor 550a is attached to the upper end of blocking member 542 with a suture or the like and extends in the same tunnel or hole as the upper end of blocking member 542. Anchor 550b is attached to the lower end of blocking member 542 with a suture or the like and extends in the same tunnel or hole as the lower end of blocking member 542. In the illustrated embodiment, anchors 550a, 550b include wings or barbs extending laterally therefrom to resist pullout from the vertebral body in which the anchor is engaged.

Figure 23A:
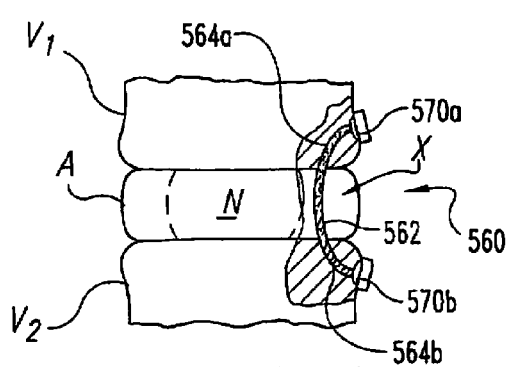
FIGS. 23A-23B are a side view and elevation view, respectively, in partial section of another embodiment annulus repair system engaged in an annulus defect.
Figure 23B:
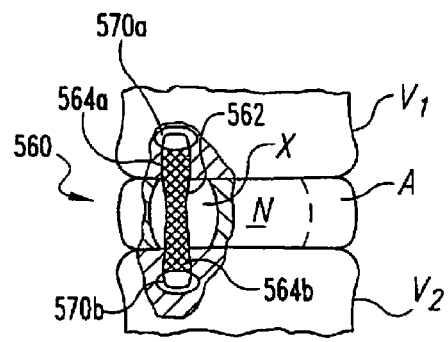

FIGS. 23A and 23B show a repair system 560 including blocking member 562 and an attachment portion including anchors 570a, 570b. In order to attach blocking member 562 to vertebrae V1 and V2, blocking member 562 is positioned in defect X with its first end 564a positioned in a tunnel or hole formed from the endplate of vertebra V1 through the body and opening at a face of vertebra V1. The second end 564b of blocking member 562 is positioned in a tunnel or hole formed from the endplate of vertebra V2 through the body and opening at a face of vertebra V2. Anchor 570a is coupled to first end 564a and abuts against the face of vertebra V1 adjacent the tunnel opening. Anchor 570b is coupled to second end 564b and abuts against the face of vertebra V2 adjacent the tunnel opening. In one form, it is contemplated that anchors 570a, 570b are buttons having a thread or attachment loop extending therefrom engaged to the attachment portion of blocking member 562 in the tunnels formed in vertebrae V1 and V2. In another form, the implant is placed through a hole in the anchor and secured thereto by knotting the ends of the implant or tying the ends of the implant to the anchor with sutures or the like.

Figure 24A:
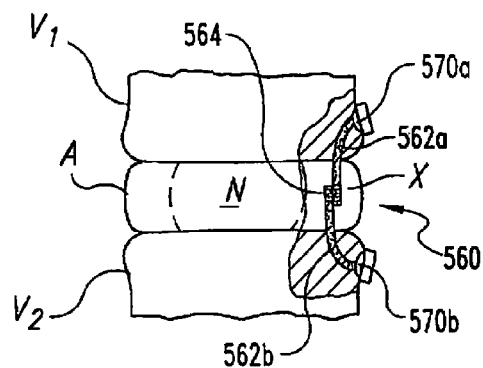
FIGS. 24A-24B are a side view and elevation view, respectively, in partial section of another embodiment annulus repair system engaged in an annulus defect.
Figure 24B:
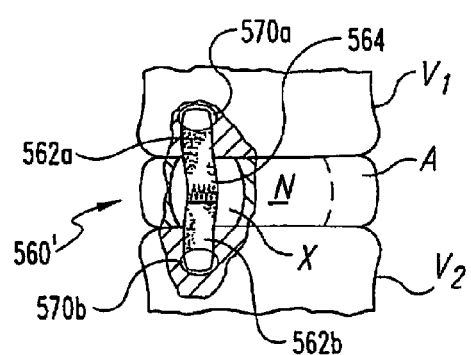

FIGS. 24A and 24B show a repair system 560' similar to repair system 560. However, blocking member 562 is includes an upper portion 562a and separate a lower portion 562b. Upper portion is attached to lower portion 562b at mid portion 564 after engagement of the upper portion 562a and lower portion 562b with respective ones of the vertebrae V1, V2. It is contemplated that attachment can be made with sutures, tying or knotting the end portions together, thermal welding or fusing the ends together, or attaching the end with fasteners or the like.

Figure 25A:
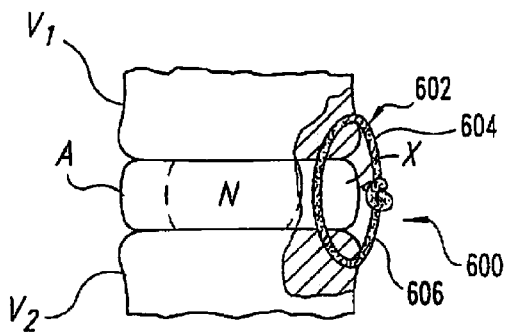
FIGS. 25A-25B are a side view and elevation view, respectively, in partial section of another embodiment annulus repair system engaged in an annulus defect.
Figure 25B:
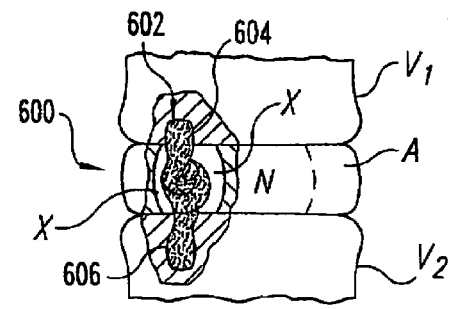

FIGS. 25A and 25B show a repair system 600 including blocking member 602 in defect X. In order to attach blocking member 602 to vertebrae V1 and V2, blocking member 602 is positioned in defect X with its first end 604 positioned in a tunnel or hole formed from the endplate of vertebra V1 through the vertebral body and opening at a face of vertebra V1. The second end 606 of blocking member 602 is positioned in a tunnel or hole formed from the endplate of vertebra V2 through the vertebral body and opening at a face of vertebra V2. Blocking member 602 is looped along the faces of vertebrae V1 and V2 so that ends 604, 606 are adjacent to and tied to one another. It is contemplated that tying can be made with sutures or knotting the end portions together.

Figure 26A:
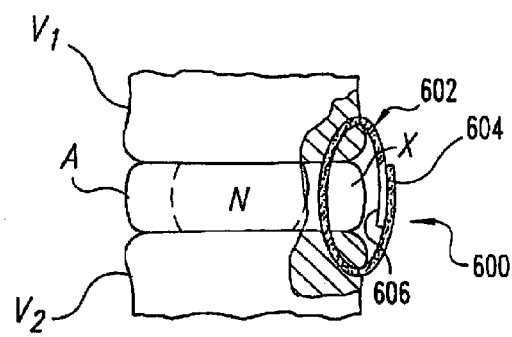
FIGS. 26A-26B are aside view and elevation view, respectively, in partial section of another embodiment annulus repair system engaged in an annulus defect.
Figure 26B:
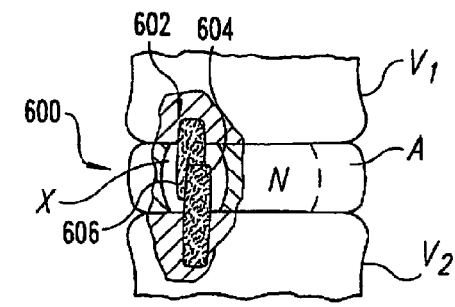
Figure 27A:
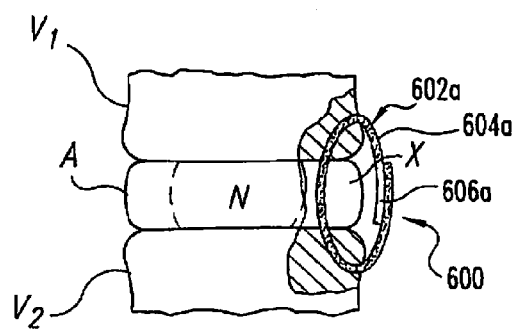
FIGS. 27A-27B are a side view and elevation view, respectively, in partial section of another embodiment annulus repair system engaged in an annulus defect.
Figure 27B:
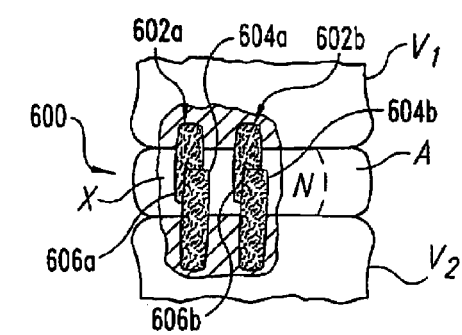

In FIGS. 26A and 26B, repair system 600 is provided with the end portions 604, 606 of blocking member 602 attached to one another in order to attach blocking member 602 to vertebrae V1 and V2. Contemplated attachment means include thermal welding or fusing the ends together, sewing the ends together, or fastening the ends together with staples, tacks, screws or the like. In FIGS. 27A and 27B repair system 600 includes two blocking members 602a and 602b in defect X and attached to vertebrae V1 and V2 as discussed above.

Figure 28:
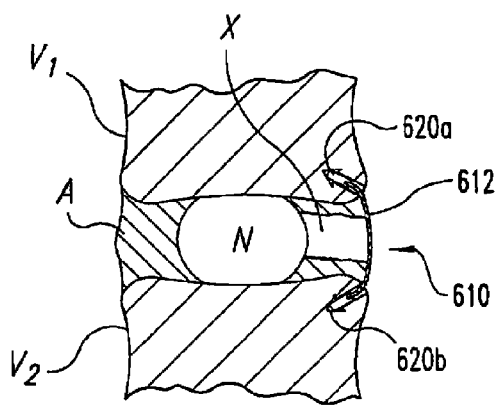
FIG. 28 is a side section view of another embodiment annulus repair system engaged adjacent to an annulus defect.

In FIGS. 28-31 there are shown various means for attaching blocking members adjacent annulus defect X and along the face of vertebrae V1 and V2. In FIG. 28, repair system 610 includes blocking member 612 adjacent defect X and extending along vertebrae V1 and V2. In order to attach blocking member 612 to vertebrae V1 and V2, the ends of blocking member 612 extend into tunnels or bores formed in vertebrae V1 and V2, and are attached to respective ones of vertebrae V1 and V2 with anchors 620a and 620b. Anchors 620a, 620b are positioned in tunnels or bores formed in the vertebral bodies V1 and V2 along with the portion of blocking member 612 attached thereto.

Figure 29:
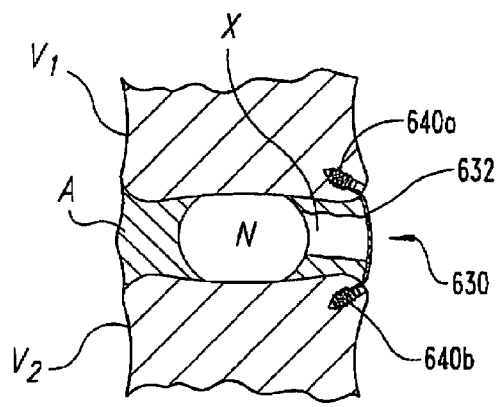
FIG. 29 is a side section view of another embodiment annulus repair system engaged adjacent to an annulus defect.

In FIG. 29, repair system 630 includes blocking member 632 extending adjacent defect X along vertebrae V1 and V2. In order to attach blocking member 632 to vertebrae V1 and V2, the ends of blocking member 632 are embedded in tunnels or bores formed in vertebrae V1 and V2 and engaged therein with interference screws 640a and 640b.

Figure 30:
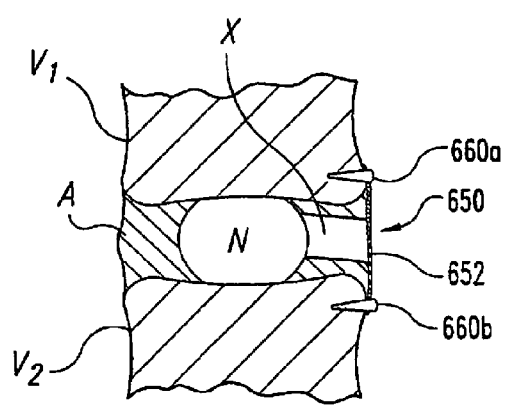
FIG. 30 is a side section view of another embodiment annulus repair system engaged adjacent to an annulus defect.
Figure 31:
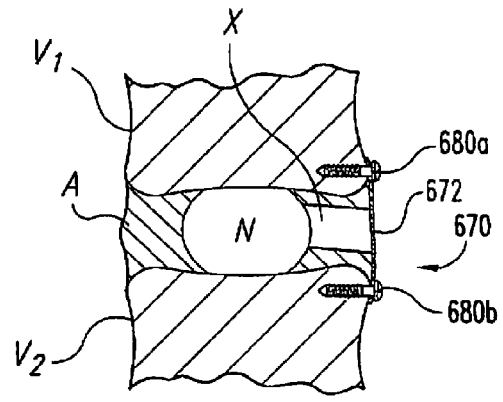
FIG. 31 is a side section view of another embodiment annulus repair system engaged adjacent to an annulus defect.

In FIG. 30, repair system 650 includes blocking member 652 extending adjacent defect X along vertebrae V1 and V2. In order to attach blocking member 652 to vertebrae V1 and V2, the ends of blocking member 652 are attached to the faces of vertebrae V1 and V2 with tacks or staples 660a and 660b. In FIG. 31, repair system 670 includes blocking member 672 extending adjacent defect X along vertebrae V1 and V2. In order to attach blocking member 672 to vertebrae V1 and V2, the ends of blocking member 672 are attached to the faces of vertebrae V1 and V2 with bone screws 680a and 680b.

Referring now to FIGS. 32A through 32D, various embodiments of blocking members are designated generally at 690. Blocking member 690 has a configuration for connection to hard tissue, such as the bony vertebral bodies V1 and V2. Blocking member 690 can be secured to the vertebral bodies adjacent annulus defect X via anchors to maintain the positioning of blocking member 690 in or adjacent the defect.

Figures 32A, 32B, 32C, 32D:
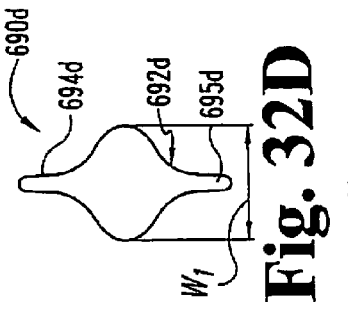
FIGS. 32A-32D illustrate various embodiments of a blocking member comprising part of an annulus repair system attachable to hard, bony tissues.

In FIG. 32A blocking member 690a includes a body portion 692a extending between an upper end 694a and a lower end 695a. Blocking member 690a includes a rectangular or square shape. Upper end 694a can be provided with a pair of upper holes 696a, and lower end 695a can be provided with a pair of lower holes 697a. Anchors, screws, staples, pins, fasteners or other attachment means can be positioned through holes 696a, 697a or coupled to the ends of blocking member 690a to engage blocking member 690a to vertebrae V1 and V2 adjacent to or in defect X.

In FIG. 32B blocking member 690b includes a body portion 692b extending between an upper end 694b and a lower end 695b. Blocking member 690b includes an oval shape, although other shapes are also contemplated. Upper end 694b can be provided with an upper hole 696b, and lower end 695b can be provided with a lower hole 697b. Anchors, screws, staples, pins, fasteners or other attachment means can be positioned through holes 696b, 697b or coupled to the ends of blocking member 690b to engage blocking member 690b to vertebrae V1 and V2.

In FIG. 32C blocking member 690c includes a body portion 692c extending between an upper end 694c and a lower end 695c. Blocking member 690c includes an oval shape, although other shapes are also contemplated. Anchors, screws, staples, pins, fasteners or other attachment means can be positioned directly through respective ones of the upper end 694c and lower end 695c, or the upper and lower ends can be coupled to anchors that engage blocking member 690c to vertebrae V1 and V2.

In FIG. 32D blocking member 690d includes a body portion 692d having an upper tab 694d with an elongated, reduced width shape extending upwardly from body portion 692d. Body portion 692d also includes a lower tab 695d having an elongated, reduced width shape extending downwardly from body portion 692d. These elongated, reduced width tabs can be attached to or engaged by an interference screw or other embedded anchor with tabs at least partially embedded into vertebrae V1, V2 along with the anchor, such as shown in FIGS. 20A and 20B, FIGS. 21A and 21B, and FIGS. 22A and 22B. The tabs can also be coupled to the anchors described herein for engagement with vertebrae V1 and V2.

Figures 33A, 33B, 33C, 33D:
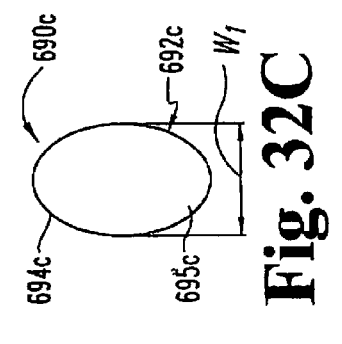
FIGS. 33A-33D illustrate various embodiments of a blocking member comprising part of an annulus repair system attachable to soft tissues.

In FIGS. 33A through 33D, there are shown various embodiments of a blocking member 700 connectable with the adjacent annulus tissue surrounding annulus defect X. In FIG. 33A blocking member 700a includes a body portion 702a having a first lateral tab 704a with a rectangular shape and an opposite second lateral tab 705a with a rectangular shape, each extending laterally outwardly from body portion 702a. Lateral tabs 704a, 705a can be engaged to the annulus tissue adjacent annulus defect X with sutures, staples, or other suitable attachment means. It is contemplated that height H1 of body portion 702a need not extend along the entire height H (FIG. 4A) of defect X between vertebra V1 and V2. In one embodiment, height H1 is less than 90 percent of the height of defect X. In another embodiment, height H1 is less than 50 percent of the height of defect X.

In FIG. 33B blocking member 700b includes a body portion 702b having a first lateral tab 704b with a semi-circular or rounded end shape and an opposite second lateral tab 705b with a semi-circular or rounded end shape. Lateral tabs 704b, 705b can be engaged to the annulus tissue adjacent annulus defect X with sutures, staples, or other suitable attachment means. It is contemplated that height H1 of body portion 702b can be provided as discussed above with respect to blocking member 700a.

In FIG. 33C blocking member 700c includes a body portion 702c having a first lateral tab 704c with a semi-circular or rounded end shape and an opposite second lateral tab 705c with a semi-circular or rounded end shape. Lateral tabs 704c, 705c taper to a reduced height configuration at the middle of body portion 702c forming a figure-eight shape. Lateral tabs 704c, 705c can be engaged to the annulus tissue adjacent annulus defect X with sutures, staples, or other suitable attachment means. It is contemplated that height H1 of body portion 702c can be provided as discussed above with respect to blocking member 700a.

In FIG. 33D blocking member 700d includes a body portion 702d having a first lateral tab 704d with a pair of laterally extending flanges 706d at the end of the tab. Body portion 702d includes an opposite second lateral tab 705d having a pair of laterally extending flanges 707d at the end of the tab. The lateral flanges on lateral tabs 704d, 705d provide extensions that add perimeter length for suture attachment. Lateral tabs 704d, 705d taper to a reduced height configuration at the middle of body portion 702d forming a figure-eight shape. Lateral tabs 704d, 705d can be engaged to the annulus tissue adjacent annulus defect X with sutures, staples, or other suitable attachment means. It is contemplated that height H1 of body portion 702d can be provided as discussed above with respect to blocking member 700a.

Figures 34A, 34B, 34C, 34D:
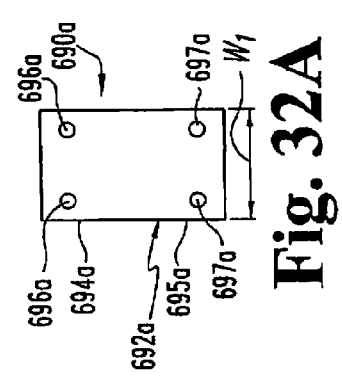
FIGS. 34A-34D illustrate various embodiments of a blocking member comprising part of an annulus repair system attachable to both hard and soft tissues.

Referring now to FIGS. 34A through 34D various embodiments of a blocking member 800 connectable to both hard tissue and soft tissue using the attachment techniques discussed above. In FIG. 34A blocking member 800a has a body portion 802a with an upper tab 804a and an opposite lower tab 805a for engagement with hard tissue. Upper tab 804a has a hole 808a to receive or to facilitate attachment to an anchor, and lower tab 805a has a hole 809a to receive or facilitate attachment to an anchor. Body portion 802a includes opposite laterally extending tabs 806a, 807a for attachment to the soft tissue surrounding the defect. The upper and lower tabs and lateral tabs together form an octagonal shape in the FIG. 34A embodiment.

In FIG. 34B blocking member 800b has a body portion 802b with an upper tab 804b and an opposite lower tab 805b for engagement with hard tissue. Upper tab 804b has a hole 808b to receive or to facilitate attachment to an anchor, and lower tab 805b has a hole 809b to receive or facilitate attachment to an anchor. Body portion 802b includes opposite laterally extending tabs 806b, 807b for attachment to the soft tissue surrounding the defect. The upper and lower tabs and lateral tabs together form a cross shape in the FIG. 34B embodiment.

In FIG. 34C blocking member 800c has a body portion 802c with an upper tab 804c and an opposite lower tab 805c for engagement with hard tissue. Upper tab 804c has a hole 808c to receive or to facilitate attachment to an anchor, and lower tab 805c has a hole 809c to receive or facilitate attachment to an anchor. Body portion 802c includes opposite laterally extending tabs 806c, 807c for attachment to the soft tissue surrounding the defect. The upper and lower tabs and lateral tabs together form an arcuate or curvilinear cross shape in the FIG. 34C embodiment.

In FIG. 34D blocking member 800d has a body portion 802d with an upper tab 804d and lower tab 805d. Tabs 804d, 805d have an elongated, reduced width configuration for embedding into the vertebrae V1, V2 as discussed above with respect to the embodiment of FIG. 32D. Body 802d also includes first lateral portion 806d and opposite second lateral portion 807d for attachment to the soft tissue surrounding the annulus defect.

The blocking member embodiments of FIGS. 32A-D and 34A-D can be provided with a body portion having a width as discussed above with respect to blocking member 50. Furthermore, the blocking member embodiments of FIGS. 34A-D can be provided with a height as discussed with respect to blocking member 700a.

While embodiments of the invention have been illustrated and described in detail in the drawings and foregoing description, the same is to be considered as illustrative and not restrictive in character, it being understood that all changes and modifications that come within the spirit of the invention are desired to be protected.

What is claimed is:

1. An instrument for inserting an annulus repair system at a defect in an annulus of a spinal disc, comprising:
   an actuating member; and
   a mounting member upon which the annulus repair system is mounted, said mounting member being positioned in said actuating member and comprising a driver member extending between upper and lower driving portions, said driver member being convexly curved between said upper and lower driving portions, said driver member being engageable with the annulus repair system to move the annulus repair system into engagement with at least one vertebra adjacent the defect.

2. The instrument of claim 1, wherein said mounting member is movable relative to said actuating member.

3. The instrument of claim 1, wherein said driving portion is engageable with the annulus repair system to move the annulus repair system into contact with said actuating member.

4. The instrument of claim 1, wherein said mounting member is movable linearly relative to said actuating member to move the annulus repair system to a first actuated position in engagement with the at least one vertebra.

5. The instrument of claim 4, wherein said mounting member is rotatable relative to the annulus repair system to move the annulus repair system from said first actuated position to a second actuated position in engagement with the at least one vertebra.

6. The instrument of claim 1, wherein said actuating member includes a retaining member engageable with the annulus repair system on the mounting member.

7. The instrument of claim 1, wherein said mounting member comprises an upper mounting surface opposite a lower mounting surface, said mounting member defining a first concavely curved portion between said lower driving portion and said upper mounting surface and a second concavely curved portion between said upper driving portion and said lower mounting surface.

8. The instrument of claim 7, wherein said upper and lower mounting surfaces are each planar.

9. The instrument of claim 7, wherein said actuating member comprises an upper actuating surface and a lower actuating surface, said upper and lower actuating surface each being concavely curved.

10. The instrument of claim 9, further comprising said annulus repair system, wherein said annulus repair system includes a first anchor comprising a body extending between a first end and a second end, said first end comprising a first end surface between top and bottom surfaces of said body, said first end surface being convexly curved and configured to engage one of said first and second concavely curved portions.

11. The instrument of claim 10, wherein said second end comprises a second end surface between said top and bottom surfaces, said second end surface being convexly curved and configured to engage one of said upper and lower mounting surfaces.

12. The instrument of claim 11, wherein said body comprises a notch extending through said top surface and said second end surface and said actuating member comprises an upper retainer and a lower retainer that are each movable relative to said actuating member, one of said upper and lower retainers being configured for disposal in said notch.

13. The instrument of claim 10, wherein said body comprises a receptacle extending through said top surface, said receptacle including a pin disposed therein, said pin being coupled to a blocking member.

14. An instrument for inserting an annulus repair system at a defect in an annulus of a spinal disc, comprising:
an actuating member having an upper actuating surface and a lower actuating surface, said actuating member engageable with the annulus repair system to move the annulus repair system into engagement with at least one vertebra adjacent the defect; and
a mounting member movably positioned in the actuating member, upon which the annulus repair system is mounted, said mounting member having an upper mounting surface and a lower mounting surface; and
a driving member disposed on a distal mounting portion of said mounting member, said driving member extending between upper and lower driving portions, said driver member being convexly curved between said upper and lower driving portions.

15. The instrument of claim 14, wherein the upper mounting surface and the lower mounting surface extend parallel to each other.

16. The instrument of claim 14, Wherein the upper actuating surface and the lower actuating surface are concavely shaped.

17. The instrument of claim 14, wherein the actuating member further includes an upper retainer and a lower retainer moveable relative to said actuating member.

18. The instrument of claim 14, wherein the driving member comprises an upper driving portion and a lower driving portion each having a proximally oriented driving surface.

19. An instrument for inserting an annulus repair system at a defect in an annulus of a spinal disc, comprising:
an actuating member having, said actuating member engageable with the annulus repair system to move the annulus repair system into engagement with at least one vertebra adjacent the defect; and
a mounting member movably positioned in the actuating member, upon which the annulus repair system is mounted, said mounting member having an upper mounting surface and a lower mounting surface opposite said upper mounting surface, the mounting member comprising a driver member extending between upper and lower driving portions, said driver member being convexly curved between said upper and lower driving portions; and
an anchor mounted to the mounting member, the anchor being configured to have a first actuated position and a second actuated position.

20. The instrument of claim 19, wherein the mounting member comprises a camming surface to push against the anchor to engage the second actuated position.

* * * * *